US006680174B1

(12) United States Patent
Matzuk et al.

(10) Patent No.: US 6,680,174 B1
(45) Date of Patent: Jan. 20, 2004

(54) ASSAY FOR GROWTH DIFFERENTIATION FACTOR 9

(75) Inventors: Martin M. Matzuk, Pearland, TX (US); Julia A. Elvin, Houston, TX (US); Pei Wang, Houston, TX (US)

(73) Assignee: Baylor College of Medicine, Houston, TX (US)

(*) Notice: Subject to any disclaimer, the term of this patent is extended or adjusted under 35 U.S.C. 154(b) by 0 days.

(21) Appl. No.: 09/283,909

(22) Filed: Apr. 1, 1999

Related U.S. Application Data
(60) Provisional application No. 60/080,385, filed on Apr. 1, 1998.

(51) Int. Cl.[7] .................. G01N 33/567; C12N 9/48; C12N 9/72; C12N 9/68; A61K 49/00
(52) U.S. Cl. .................. 435/7.21; 435/7.2; 435/212; 435/215; 435/217; 424/9.2; 530/399; 530/324; 530/350
(58) Field of Search .................. 435/7.2, 7.21, 435/212, 215, 217; 424/9.2; 530/399, 324, 350

(56) References Cited

U.S. PATENT DOCUMENTS 5,821,056 A  10/1998  Lee

FOREIGN PATENT DOCUMENTS

WO   WO 94/15966   7/1994

OTHER PUBLICATIONS

Letterio et al., Mineral and Electrolyte Metabolism, 1998, vol. 24, pp. 161–167.*
Alberts et al. Molecular Biology of the cell 2nd Edition, 1989, section 10–25.*
Stedman's Medical Dictionary, 1995.*
Salustri, A., et al., "Endocrine and paracrine regulation of cumulus expansion", Zygote, 4:313–315. (1996).
Vanderhyden, B.C., et al., "Mouse Oocytes Regulate Granulosa Cell Steroidogenesis", Endocrin., 133(1):423–426 (1993).
Eppig, J.J., et al., "Murine Oocytes Suppress Expression of Luteinizing Hormone Receptor Messenger Ribonucleic Acid by Granulosa Cells", Biol. Reprod., 56:976–984 (1997).
Nekola, M.V., and Nalbandov, A.V., "Morphological Changes of Rat Follicular Cells as Influenced by Oocytes", Biol. Reprod., 4:154–160 (1971).
El–Fouly, M.A., et al., "Role of the Ovum in Follicular Luteinization", Endocrin., 87:288–293 (1970).
Dong, J., et al., "Growth Differentiation Factor–9 is Required During Early Ovarian Folliculogenesis", Nature, 383:531–535 (1996).

Buccione, R., et al., "FSH–Induced Expansion of the Mouse Cumulus Oophorus in Vitro is Dependent upon a Specific Factor(s) Secreted by the Oocyte", Develop. Biol., 38:16–25 (1990).
Salustri A., et al., "Hyaluronic Acid Synthesis by Mural Granulosa Cells and Cumulus Cells in Vitro is Selectively Stimulates by a Factor Produced by Oocytes and by Transforming Growth Factor–β", J. Biol. Chem., 265(32):19517–19523 (1990).
Fülop, C., et al., "Coding Sequence of a Hyaluronan Synthase Homologue Expressed during Expansion of the Mouse Cumulus–Oocyte Complex", Arch. Biochem. Biophys., 337(2):261–266 (1997).
Spicer, A.P., et al., "Molecular Cloning and Characterization of a Putative Mouse Hyaluronan Synthase", J. Biol. Chem., 271(38):23400–23406 (1996).
Canipari, R., et al., "Mouse Oocytes Inhibit Plasminogen Activator Production by Ovarian Cumulus and Granulosa Cells", Develop. Biol., 167:371–378 (1995).
Oonk, R.B., et al., "Cyclic AMP–dependent and –independent Regulation of Cholesterol Side Chain Cytochrome P–450 (P–450$_{scc}$) in Rat Ovarian Granulosa Cells and Corpora Lutea", J. Biol. Chem., 264(36):21934–21942 (1989).
Incerti, B., et al., "Stucture of the mouse growth/differentiation factor 9 gene", Biochim. Biophys. Acta., 1222:125–128 (1994).
McGrath, S.A., et al., "Oocyte–Specific Expression of Growth/Differentiation Factor–9", Mol. Endo., 9(1):131–136 (1995).
McPherron, A.C. and Lee, S.–J., "GDF–9 and GDF–9: Two New Members of the Transforming Growth Factor–β Superfamily Containing a Novel Pattern of Cysteines", J. Biol. Chem., 268(5):3444–3449 (1993).
Salustri, A., et al., "Synthesis and Accumulation of Hydaluronic Acid and Proteoglycans in the Mouse Cumulus Cell–Oocyte Complex during Follicle–stimulating Hormone–induced Mucification", J. Biol. Chem., 264(23):13840–13847 (1989).

(List continued on next page.)

Primary Examiner—Yvonne Eyler
Assistant Examiner—Janit L. Andres
(74) Attorney, Agent, or Firm—Hamilton, Brook, Smith & Reynolds, P.C.

(57) ABSTRACT

The present invention relates to a method of identifying an agent which alters (inhibits, enhances) activity of GDF-9. The method involves combining cells having a receptor for GDF-9 and a gene, wherein expression of the gene is regulated by binding of GDF-9 to the receptor; GDF-9; and an agent to be assessed. The combination produced is maintained under conditions appropriate for binding of GDF-9 to the receptors on the cells. The extent to which binding of GDF-9 to the receptors on the cells occurs is then determined, wherein binding of GDF-9 to the receptor to a lesser or greater extent in the presence of the agent to be assessed than in its absence, is indicative of an agent which alters GDF-9 activity.

51 Claims, 6 Drawing Sheets

OTHER PUBLICATIONS

Tirone, E., et al., "Hyaluronan Synthesis by Mouse Cumulus Cells in Regulated by Insterations between Follicle–stimulating Hormone (or Epidermal Growth Factor) and a Soluble Oocyte Factor (or Transforming Growth Factor $\beta_1$)", *J. Biol. Chem.*, 272(8):4787–4794 (1997).

Salustri, A., et al., "Mouse Oocytes Regulate Hyaluronic Acid Synthesis and Mucification by FSH–Stimulated Cumulus Cells", *Develop. Biol.*, 138:26–32 (1990).

Richards, J.S. and Hedin, L., "Molecular Aspects of Hormone Action in Ovarian Follicular Development Ovulation, and Luteinization", *Ann. Rev. Physiol.*, 50:441–463 (1988).

Clark, B.J., et al., "Hormonal and Developmental Regulation of the Sterodiogenic Acute Regulatory Protein", *Mol. Endoc.*, 9(10):1346–1355 (1995).

Arakane, F., et al., "Phosphorylation of Steroidogenic Acute Regulatory Protein (StAR) Modulates Its Steroidogenic Activity", *J. Biol. Chem.*, 272(51):32656–32662 (1997).

Schuetz, A.W., and Dubin, N.H., "Progesterone and Prostaglandin Secretion by Ovulated Rat Cumuls Cell–Oocyte Complexes", *Endo.*, 108(2):457–463 (1981).

Eppig, J.J., et al., "Mouse Oocytes Suppress cAMP–Induced Expression of LH Receptor mRNA by Granulosa Cells in Vitro", *Mol. Reprod. Devel.*, 49:327–332 (1998).

Lim, H., et al., "Multiple Female Reproductive Failures in Cyclooxygenase 2–Deficient Mice", *Cell*, 91:137–208 (1997).

Lawrence, T.S., et al., "Binding of Human Chorionic Gonadotropin by Rat Cumuli Oophori and Granulosa Cells: A Comparative Study", *Endoc.*, 106(4):1114–1118 (1980).

Meduri, G., et al., "New Functional Zonation in the Ovary as Shown by Immunohistochemistry of Luteinizing Hormone Receptor", *Endoc.*, 131(1):366–373 (1992).

Mather, J.P., et al., "Activins, Inhibins, and Follistatins: Further Thoughts on a Growing Family of Regulators", *Proc. Soc. Exp. Biol. Med.*, 215:209–222 (1997).

Matzuk, M.M., et al., "Transgenic Models to Study the Roles of Inhibins and Activins in Reproduction, Oncogenesis, and Development", *Recent Prog. Horm. Res.*, 51:123–157 (1996).

Packer, A.I., et al., "The Ligand of the c–kit Receptor Promotes Oocyte Growth", *Dev. Biol.*, 161:194–205 (1994).

Carabatsos, M.J., et al., "Characterization of Oocyte and Follicle Development in Growth Differentiation Factor–9 Deficient Mice", *Dev. Biol.*, 204:373–384 (1998).

Elvin, J.A., et al., "Paracrine Actions of Growth Differentiation Factor–9 in the Mammalian Ovary", *Mol. Endoc.*, 13(6):1035–1048 (1999).

Elvin, J.A., et al., "Molecular Characterization of the Follicle Defects in the Growth Differentiation Factor–9 Deficient Ovary", *Mol. Endoc.*, 13(6):1018–1034 (1999).

Eppig, J.J., et al., "Oocyte control of granulosa cell development: how and why", *Hum. Reprod.*, 12 Natl. Suppl., JBFS, 2(2):127–132 (1997).

Salustri, A., et al., "Oocyte–Granulosa Cell Interactions", "The Ovary",edited by Eli Y. Adashi & Peter C.K. Leung, Raven Press, Ltd., NY (1993).

Chen, L., et al., "Functional significance of cumulus expansion in the mouse: roles for the preovulatory synthesis of hyaluronic acid within the cumulus mass", *Mol. Reprod. Dev.*, 34:87–93 (1993).

Elvin, J.A and Matzuk, M.M., "Mouse models of ovarian failure", *Rev. Reprod.*, 3:183–195 (1998).

Hizaki, H., et al., "Abortive expansion of the cumulus and impaired fertility in mice lacking the prostaglandin E receptor subtype EP(2)", *Proc. Natl. Acad. Sci. USA*, 96:10501–10506 (1999).

Kennedy, C.R. et al., "Salt–sensitive hypertension and reduced fertility in mice lacking the prostaglandin $EP_2$ receptor", *Nature Med.*, 5: 217–220 (1999).

Lydon, J.P., et al., "Mice lacking progestrone receptor exhibit pleitropic reproductive abnormalities", *Genes Dev.*, 9:2266–2278 (1995).

Tilley, S.L., et al., "Reproductive failure and reduced blood pressure in mice lacking the EP2 prostaglandin E2 receptor", J. Clin. Invest., 103:1539–1545 (1999).

\* cited by examiner

ASSAY FOR GROWTH DIFFERENTIATION FACTOR 9

RELATED APPLICATION(S)

This application claims priority to provisional Application No. 60/080,385, filed Apr. 1, 1998, the entire teachings of which are incorporated herein by reference.

GOVERNMENT SUPPORT

The invention was supported, in whole or in part, by NIH grants (NICHD) RO1 HD33438, GM-07330 and GM-08307. The Government has certain rights in the invention.

BACKGROUND OF THE INVENTION

The oocyte plays an integral role in regulating folliculogenesis within the mammalian ovary. In particular, the oocyte has been shown to act on granulosa cells to regulate follicle formation perinatally, stimulate granulosa cell proliferation, modulate granulosa cell gene expression, and influence steroidogenesis (Reviewed in (Eppig, J. J., *Dev. Biol.*, 5:51–59 (1994)). The granulosa cells in the pre-ovulatory follicle can be separated into two populations with regard to their proximity to the oocyte; cumulus granulosa cells closely surround the oocyte while the mural granulosa cells are located around the periphery of the follicle separated from the oocyte by an antrum. Cumulus cells secrete a hyaluronic acid-rich matrix during cumulus expansion and are extruded with the oocyte during ovulation. This expanded matrix is a critical factor for reproductive integrity since it binds the oocyte and cumulus cells together, facilitates follicular extrusion and oviductal fimbria capture, and allows sperm penetration and fertilization (Salustri, A., et al., *Zygote*, 4:313–315 (1996)). On the other hand, mural granulosa cells synthesize proteases important for follicle rupture at ovulation, remain within the ovary after the cumulus cell-oocyte complex is released, and eventually undergo terminal differentiation to form the corpus luteum. These positional and functional differences in the granulosa cell populations suggests that gradients of oocyte-secreted factors modulate gene expression and eventual cell differentiation. In vitro studies demonstrate that oocyte-secreted growth factors regulate granulosa cell synthesis of hyaluronic acid, urokinase plasminogen activator (uPA) and LH receptor as well as steroidogenesis and luteinization (Salustri, A., et al., Zygote 4:313–315 (1996); Vanderhyden, B. C., et al., *Endocrinology*, 133:423–426 (1993); Eppig, J. J., et al., *Biol. Reprod.*, 56:976–984 (1997); Eppig, J. J., et al., *Human Reprod.*, 12:127–132 (1997); Nekola, M. V. and Nalbandov, A. V., *Biol. Reprod.*, 4:154–160 (1971); El-Fouly, M. A., et al., *Endocrinology*, 87:288–293 (1970)). However, the identities of the oocyte-derived factors that regulate these somatic cell functions remain largely unknown.

Mouse growth differentiation factor 9 (mGDF-9) is expressed in the ovary and specifically in oocytes (PCT WO94/15966). A GDF-9 knockout mouse demonstrated female infertility due to an early block in folliculogenesis (Dong et al., *Nature*, 383:531–535 (1996)), however, the GDF-9 receptor and the cell type expressing the GDF-9 receptor have not been identified. Discovery of the cell type expressing the GDF-9 receptor would assist in defining the role of GDF-9 in fertility, and would provide an assay system for identifying agents which target GDF-9 activity.

SUMMARY OF THE INVENTION

Described herein is an in vitro assay for growth differentiation factor 9 (GDF-9) based upon the discovery that GDF-9 binds to granulosa cells found in the ovary of mammals. As also described herein, expression of particular proteins are enhanced and/or inhibited upon binding of GDF-9 to the receptors on the granulosa cells.

The present invention relates to a method of identifying an agent which alters (modulates) activity of GDF-9. As used herein the term "alters" refers to partial and/or complete inhibited activity (decreased activity) or enhanced activity (increased activity). The method involves combining cells having receptors for GDF-9 (e.g., granulosa cells) and a gene (one or more) whose expression is regulated by binding of GDF-9 to the receptors (e.g., hyaluronan synthase, steroidogenic acute regulatory protein (StAR), luetinizing hormone (LH) receptor, cyclooxygenase 2 (COX-2), urokinase plasminogen activator (uPA), kit ligand, activin/inhibin βB and follistatin); GDF-9; and an agent to be assessed (test sample). The combination produced in the test sample is maintained under conditions appropriate for binding of GDF-9 to the receptors on the cells. The extent to which expression of the gene occurs is then determined, wherein alteration of expression of the gene upon binding of GDF-9 to the receptors in the presence of the agent to be assessed indicates that the agent alters GDF-9 activity. The method can further comprise a control step wherein the extent to which binding occurs in the presence of the agent is compared to the extent to which binding occurs in the absence of the agent. For example, the extent to which expression of the gene occurs in the test sample is compared to the extent to which expression of the gene occurs in a control sample (e.g., a combination comprising the cells having receptors for GDF-9 and a gene whose expression is regulated by binding of GDF-9 to the receptors, and GDF-9).

The present invention also relates to a method of identifying an agent which is an inhibitor of GDF-9 activity. In one embodiment, granulosa cells; GDF-9; and an agent to be assessed are combined. The combination produced is maintained under conditions appropriate for binding of GDF-9 to receptors on the granulosa cells; and the extent to which expression of a gene regulated by binding of GDF-9 to the receptors occurs upon binding of GDF-9 to the receptors on the granulosa cells is determined. Inhibition of expression of the gene upon binding of GDF-9 to the receptors in the presence of the agent to be assessed indicates the agent inhibits GDF-9 activity. In another embodiment, granulosa cells; GDF-9; and an agent to be assessed are combined. The combination produced is maintained under conditions appropriate for binding of GDF-9 to receptors on the granulosa cells; and the extent to which expression of uPA, a gene regulated by binding of GDF-9 to the receptors, occurs upon binding of GDF-9 to the receptors on the granulosa cells is determined. Increased expression of the uPA gene upon binding of GDF-9 to the receptors in the presence of the agent to be assessed indicates that the agent inhibits GDF-9 activity.

The present invention also relates to a method of identifying an agent which is an enhancer of GDF-9 activity. In one embodiment, granulosa cells; GDF-9; and an agent to be assessed are combined. The combination produced is maintained under conditions appropriate for binding of GDF-9 to receptors on the granulosa cells and the extent to which expression of a gene regulated by binding of GDF-9 to the receptors occurs upon binding of GDF-9 to the receptors on the granulosa cells is determined. Enhanced expression of the gene upon binding of GDF-9 to the receptors in the presence of the agent to be assessed is indicative of an agent which is an enhancer of GDF-9 activity. In another embodiment, granulosa cells; GDF-9; and an agent to be assessed are combined. The combination produced is maintained under conditions appropriate for binding of GDF-9 to receptors on the granulosa cells; and the extent to which expression of a uPA gene regulated by binding of GDF-9 to the receptors occurs upon binding of GDF-9 to the receptors on the granulosa cells is determined. Decreased expression of the uPA gene upon binding of GDF-9 to the receptors in the presence of the agent to be assessed indicates that the agent enhances GDF-9 activity.

The methods of the present invention can also be used to identify an agent which inhibits fertility in a mammal (e.g., human). Alternatively, the methods of the present invention can be used to identify an agent which enhances fertility in a mammal.

The present invention also relates to a method of identifying an agent which is an agonist of GDF-9. In this method, cells having receptors for GDF-9 and a gene, wherein expression of the gene is regulated by binding of GDF-9 to the receptor; GDF-9; and an agent to be assessed are combined. The combination produced is maintained under conditions appropriate for binding of GDF-9 to receptors on the cells, and the extent to which expression of the gene regulated by binding of GDF-9 to the receptors occurs is determined, wherein expression of the gene in the presence of the agent to be assessed indicates that the agent is an agonist of GDF-9.

In addition, the present invention relates to a method of identifying an agent which is an agonist or antagonist of GDF-9. In this method, cells having receptors for GDF-9 and a gene whose expression is regulated by binding of GDF-9 to the receptor; GDF-9 and an agent to be assessed are combined. The combination produced is maintained under conditions appropriate for binding of the agent to receptors on the cells. The extent to which binding of the agent to the receptors on the cells occurs is determined, wherein binding of the agent to the GDF-9 receptors indicates that the agent is an agonist or an antagonist of GDF-9.

The extent to which binding of GDF-9 to the receptor on the cells occurs can be determined in a variety of ways. For example, the extent to which binding occurs is determined by directly measuring a gene product (e.g., nucleic acids such as DNA, RNA of the gene; protein, peptide encoded by the gene) of the gene which is regulated by binding of GDF-9 to the receptors. In one embodiment, the gene encodes a protein involved in the synthesis of hyaluronic acid (e.g., hyaluronan synthase), and the extent to which binding of GDF-9 to the receptors on the granulosa cells occurs is determined by measuring the production of a product of the gene (e.g., RNA coding for hyaluronan synthase), wherein an increase in production the gene product indicates the agent is an enhancer of GDF-9 activity and a decrease of production of gene product indicates the agent is an inhibitor of GDF-9 activity. In another embodiment, the gene encodes a protein involved in the synthesis of progesterone (e.g., StAR), and the extent to which binding of GDF-9 to the receptors on the granulosa cells occurs is determined by measuring the production of a product of the gene (e.g., RNA coding for StAR), wherein an increase in the production of the gene product indicates that the agent is an enhancer of GDF-9 activity, and a decrease in production of the gene product indicates that the agent is an inhibitor of GDF-9 activity. In yet another embodiment, the gene encodes a protein involved in the production of plasmin (e.g., uPA), and the extent to which expression of the gene regulated by binding of GDF-9 to the receptors occurs upon binding of GDF-9 to the receptors is determined by measuring the production of a product of the gene (e.g., RNA coding for uPA), wherein a decrease in the expression of the gene product indicates the agent is an enhancer of GDF-9 activity, and an increase in expression of the gene product indicates the agent is an inhibitor of GDF-9 activity. The extent to which binding of GDF-9 to the receptor on the cells occurs can also be determined by measuring a product or function (e.g., hyaluronic acid, progesterone and/or plasmin) attributed to the activity of proteins encoded by the gene whose expression is regulated by binding of GDF-9 to the receptor on the cell.

The findings that granulosa cells respond to GDF-9 and that this response can be determined by means of one or more inducible genes allows for an in vitro bioassay for GDF-9. Such an assay can be used to diagnose fertility problems in mammals, and identify inhibitors, enhancers, antagonists and analogues of GDF-9 which can be used, for example, to diagnose and/or treat fertility problems in mammals.

DETAILED DESCRIPTION OF THE INVENTION

Figure 1:
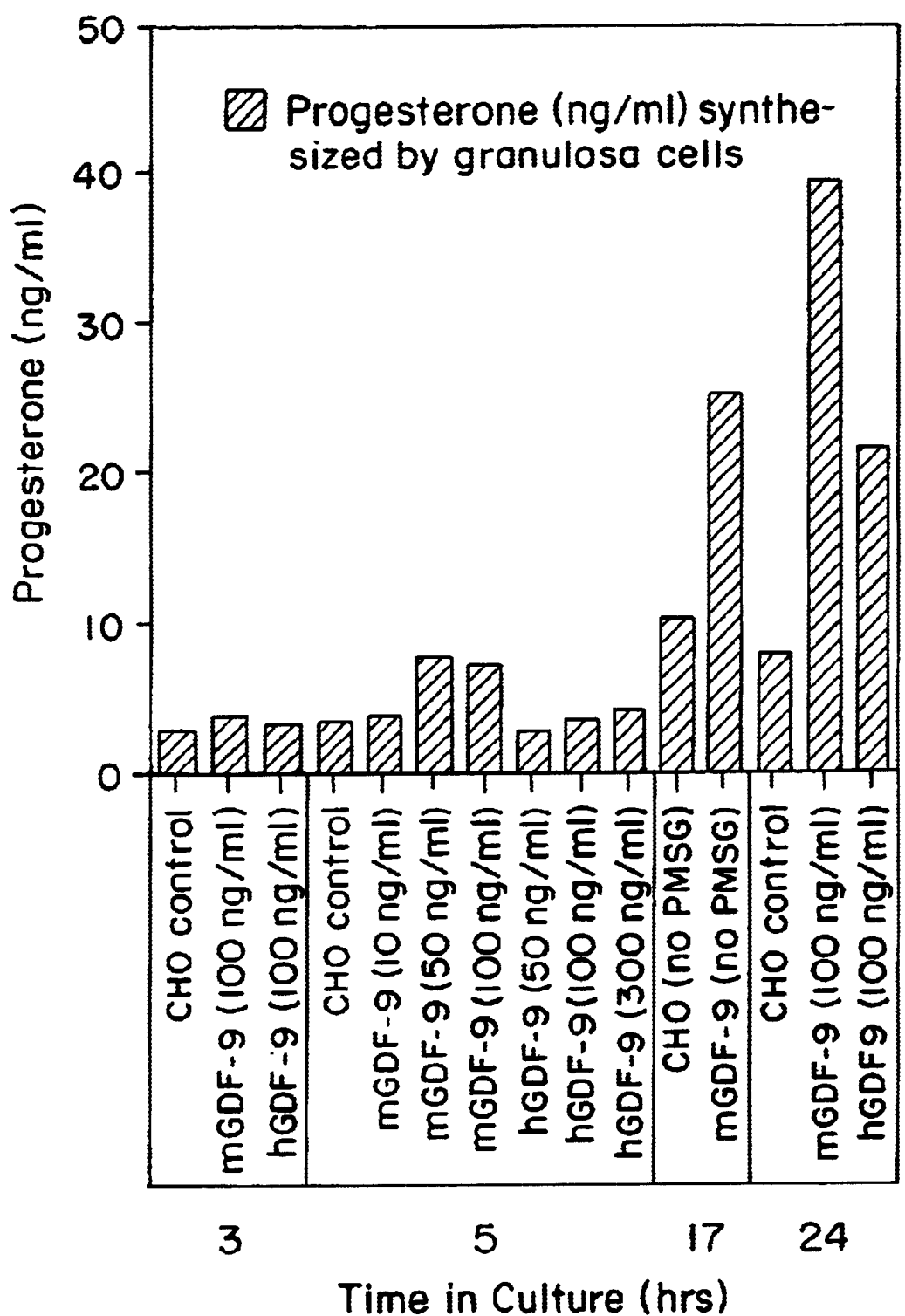
FIG. 1 is a bar graph of the results of a progesterone radioimmunoassay showing that conditioned media containing recombinant mouse GDF-9 (mGDF-9) or recombinant human GDF-9 (hGDF-9) stimulated progesterone synthesis by in vitro cultured primary granulosa cells in a time and concentration dependent manner.

The present invention relates to a method of identifying an agent which alters (modulates) activity of growth differentiation factor 9 (GDF-9). In particular, the method of the present invention is an assay for assessing the ability of an agent to inhibit or enhance the activity of GDF-9, a factor required during early ovarian folliculogenesis. In the methods of the present invention in which an agent which alters (inhibits, enhances) GDF-9 activity is identified, the following reagents are combined to produce a test sample: cells having a receptor for GDF-9 and a gene whose expression is regulated by binding of GDF-9 to the receptor; GDF-9; and an agent to be assessed.

Cells having a receptor for GDF-9 and a gene whose expression is regulated by binding of GDF-9 to the receptor on the cell, include, for example, granulosa cells (e.g., mural granulosa cells, cumulus cells) found in the ovarian follicle of mammals. The ovarian follicle of a mammal, which includes oocytes surrounded by cells having receptors for GDF-9 (e.g., granulosa cells), in any phase of folliculogenesis can also be used in the methods of the present invention. For example, a primordial, primary, secondary, tertiary (preovulatory) or superovulated ovarian follicle can be used in the methods of the present invention. In this embodiment, the ovarian follicle would generally include oocytes, which expresses GDF-9, and granulosa cells. Therefore, the addition of GDF-9 in the test sample is optional in this embodiment. The extent to which the agent to be assessed inhibits the GDF-9 activity or further enhances the activity of GDF-9 present in the ovarian follicle is assessed. Granulosa cells and/or ovarian follicles can be obtained from any mammalian sources as described herein and using skills known in the art. For example, granulosa cells and/or ovarian follicles can be obtained from primate (e.g., monkey, human), bovine, porcine, feline, canine and murine sources. In addition, granulosa cells and/or ovarian follicles can be obtained from a mammal in any phase of folliculogenesis or from a mammal in a superovulated state. For example, a superovulated state in a mammal can be obtained by administering gonadotropin (e.g., pregnant mare serum gonadotropin) to the mammal, from which granulosa cells and/or ovarian follicles are being obtained. Other examples of suitable cells for use in the methods of the present invention include cells recombinantly produced to express the GDF-9 receptor and a gene whose expression is regulated by binding of GDF-9 to the receptor on the cell (e.g., recombinantly produced chinese hamster ovary (CHO) cells which express the GDF-9 receptor and, upon binding of GDF-9 to the receptor, also express hyaluronan synthase).

As described herein, the methods of the present invention utilize cells having a receptor for GDF-9 and a gene whose expression is regulated by binding of GDF-9 to the receptor on the cell. The gene (one or more) for use in the present invention includes genes which encode, for example, hyaluronan synthase, steroidogenic acute regulatory protein, luetinizng hormone receptor, cyclooxygenase 2, urokinase plasminogen activator, activin/inhibin and follistatin.

As used herein, "GDF-9" refers to GDF-9 protein, its individual subunits, multimers of its individual subunits, functional fragments or portions of GDF-9, and functional equivalents and/or analogues of GDF-9. As defined herein, functional fragments of GDF-9 are fragments which regulate a gene which encodes, for example, a protein(s) involved in synthesis of hyaluronic acid (e.g., hyaluronan synthase), a protein(s) involved in synthesis of progesterone (e.g., StAR) and/or a protein involved in the synthesis of plasmin (e.g., uPA). As also defined herein, functional equivalents or fragments of "GDF-9" include modified GDF-9 protein such that the resulting GDF-9 product has activity similar to the GDF-9 described herein (e.g., regulating a gene which encodes a protein involved in synthesis of hyaluronic acid).

GDF-9 suitable for use in the methods and compositions of the present invention can be obtained from a variety of sources or synthesized using skills known in the art. For example, GDF-9 as it occurs in an ovarian follicle can be used in the methods of the present invention. In addition, GDF-9 can be purified (isolated, essentially pure) from natural sources (e.g., mammalian sources, such as primate, bovine, porcine, feline, canine and murine sources), produced by chemical synthesis, produced by recombinant DNA techniques or obtained from commercial sources.

As described herein, the combination produced in the methods of the present invention (test sample) is maintained under conditions appropriate for binding of GDF-9 to receptors on the cells. A suitable temperature range for performing the methods described herein is from about 0° C. to about 45° C. In one embodiment, the methods can be performed at about 37° C., and in another embodiment, the methods can be performed at about 25° C. A suitable pH range at which the methods can be performed is from about pH 5 to about pH 8, and, in particular, from about pH 7 to about pH 7.4. In one embodiment, the methods can be performed at about pH 7.4. In addition, the methods can be performed in a day or over several days. For example, the methods can be performed from about 1 hour to about 96 hours, from about 1 hour to about 48 hours or from about 1 hour to about 24 hours. In one embodiment, the methods can be performed from about 3 hours to about 24 hours.

In the methods of the present invention, the extent to which binding of GDF-9 to the receptors on the cells occurs can be determined directly or indirectly. For example, the extent to which binding of GDF-9 to the receptors on the cells occurs can be determined by directly measuring the particular gene product (e.g., DNA, RNA (mRNA), peptide, protein) produced in response to binding of GDF-9 to the GDF-9 receptor present on the cells used in the assay. Examples of such particular gene products include, but are not limited to, hyaluronan synthase, steroidogenic acute regulatory protein, luetinizng hormone receptor, cyclooxygenase 2, urokinase plasminogen activator, kit ligand, activin/inhibin βB and follistatin.

Alternatively, products or functions which occur (e.g., downstream) as a result of the activity of the gene product can also be measured. In one embodiment, the gene is involved in the synthesis of hyaluronic acid (e.g., a gene coding for hyaluronan synthase) and a product which results from the activity of the gene, such as hyaluronic acid, can be measured. In another embodiment, the gene is involved in synthesis of progesterone (e.g., a gene encoding StAR) and a product which results from the activity of the gene, such as progesterone, phosphorylated StAR and/or another steroid in the progesterone synthetic pathway, can be measured. In a further embodiment, the gene is involved in the synthesis of plasmin (e.g., uPA) and a product which results from the activity of the gene, such as plasmin and/or a function of the gene, such as the breakdown of plasminogen, can be measured. In another embodiment, the gene is involved in the production of prostaglandins (e.g., COX-2) and a product which results from the activity of the gene, such as prostaglandins, can be measured. The gene can also be involved in the production of activin B or inhibin B, and a product which results from the activity of the gene, such as activin βB:activin and/or βB inhibin α:activin βB, can be measured. In another embodiment, the gene is involved in the production of LH receptor and a product which results from the activity of the gene, such as products produced as a result of the binding of LH receptor (e.g., cyclic AMP), and/or a function which results from the activity of the gene such as the binding of a ligand to the LH receptor, can be measured. In addition, particularly in the methods in which an agonist or an antagonist of GDF-9 is being identified, the extent to which binding of GDF-9 in the presence of the agent to be assessed to the receptors on the cells occurs, can be determined by measuring the amount of GDF-9 bound to receptors on the cells directly using skills known in the art (e.g., radioreceptor assays).

Methods which can be used to measure the extent to which binding of GDF-9 to the receptors on the cells occurs depends upon which parameter is being measured. The presence of nucleic acids (DNA, RNA) associated with the gene which is regulated by binding of GDF-9 to the receptor on the cell can be determined using for example, visualization of polymerase chain reaction (PCR) products, radiolabeling methods, photographing detection of radiolabeled PCR products, Southern blots of PCR products, RNase protection assays and/or Northern blots. Alternatively, the presence of protein associated with the gene which is regulated by binding of GDF-9 to the receptor on the cell can be determined using techniques such as high pressure liquid chromatography (HPLC), immunohistochemistry, Western blot analysis and immunoprecipitation. In addition, the downstream products (e.g., hyaluronic acid, progesterone, plasmin) generated in response to the activity of the gene which is regulated by binding of GDF-9 to the receptors on the cells can be measured using, for example, HPLC and/or radioimmunoassays.

The methods of the present invention can further comprise the use of a control sample. For example, the extent to which binding of GDF-9 to the receptors on the cells in the test sample is compared to the extent to which binding of GDF-9 to the receptors on the cells occurs in a control sample (i.e., a sample which includes the same combination of reagents as the test sample except for the agent to be assessed, and which has been processed in the same manner as the test sample).

The methods described herein and the agents identified by the methods can be used in a variety of ways. For example, the methods can be used as a screening method to identify agents which are inhibitors, enhancers, antagonists, agonists, and/or analogs of GDF-9 and which can be used to diagnose and/or treat reproductive problems or as a diagnostic assay for detecting reproductive problems such as infertility (e.g., an assay of follicular fluid to analyze GDF-9 activity). Agents identified by the methods of the present invention can be used in any disease or condition in which GDF-9 activity is abnormal. For example, agents identified in the methods of the present invention can be used to inhibit fertility (e.g., contraception, contraceptives) or enhance fertility (e.g., increase the success of in vitro fertilization).

As described herien, in initial follicle culture experiments using the CHO cell media conditioned with cleaved, mature mouse GDF-9 protein (CHO 19A12), it was noted that the follicles appeared granular, granulosa cells rounded up and pulled away from each other and after 2 days in culture, appeared to form a mucified matrix. CHO control media or the media containing bone morphogenetic protein 15 (BMP-15) alone (CHO 21A5) did not have this mucifying effect on the follicles. The media from cells expressing both GDF-9 and BMP-15 (CHO 27A11), but with the GDF-9 level estimated to be 5 to 10-fold lower than in CHO 19A12, eventually caused a mucification event after 5 days in culture.

Granulosa cells in immediate contact with the oocyte in the preovulatory follicle, known as cumulus cells, produce a proteoglycan matrix containing hyaluronic acid both in vivo and in vitro in a process called cumulus expansion. This expanded matrix binds the oocyte and cumulus cells together, facilitates follicular extrusion and oviductal fimbria capture, and allows sperm penetration and fertilization (Salustri et al., *Zygote*, 4:313–315 (1996)). It has been observed that in vitro cumulus expansion depends on follicle stimulating hormone and an oocyte derived factor (Buccione et al., *Dev. Biol.*, 138:16–25 (1990)). Cumulus cells stripped away from the oocyte do not expand, assume an adherent, fibroblastic appearance, and produce negligible amounts of hyaluronic acid. If oocytes are added back to the culture, or if the cumulus cells are grown in oocyte conditioned media (OCM) (~1 oocyte/$\mu$l media), they produce 5–10 fold higher levels of hyaluronic acid. It was also shown that mural granulosa cells (i.e., granulosa cells of the preovulatory follicle not in contact with the oocyte) can be induced to make hyaluronic acid in vitro by treatment with oocyte conditioned media and/or TGF-$\beta$ (Salustri et al., *J. Biol. Chem.*, 265: 19517–19523 (1990)). The effect of both OCM and TGF-$\beta$ was additive. Anti-TGF-$\beta$ antibodies were able to block the TGF-$\beta$ effect, but could not block the effect of oocyte conditioned media. This indicates that TGF-$\beta$ itself is not the oocyte-derived signal that stimulates hyaluronic acid production. Additionally, these experiments were repeated using the transcription blocking agent, Actinomycin D, and it was shown that ~50% of the effect of TGF-$\beta$ was blocked under these conditions (Tirone et al., *J. Biol. Chem.*, 272: 4787–4794 (1997)).

Recently, hyaluronan synthase type 2 (HAS2) was identified in mouse and shown to be capable of catalyzing hyaluronic acid production in transfected COS cells (Spicer et al., *J. Biol. Chem.*, 271: 23400–23406 (1996)). In another study, it was shown that 1 hour to 4 hours after the human chorionic gonadotropin (hCG) administration of a standard superovulation protocol (pregnant mare serum gonadotropin (PMSG)—48 hrs hCG), HAS2 was shown to be induced in cumulus oocyte complexes (Fulop et al., *Arch. Biochem. Biophysics*, 337:261–266 (1997)). Due to its enzymatic activity and its expression pattern, HAS2 is a likely to be responsible for the hyaluronic acid production leading to cumulus expansion, and may be the gene responding to the factor produced by the oocyte or present in oocyte conditioned media.

Additionally, studies have shown that a second gene, urokinase plasminogen activator (uPA), is inhibited by an oocyte derived factor (Canipari et al., *Devel. Biol.*, 167: 371–378 (1995)). uPA is a serine protease that cleaves plasminogen to form the active protease plasmin, and has been suggested to play a role in preovulatory proteolytic degradation of the follicle wall. uPA is stimulated by gonadotropins in granulosa cells and theca cells. Cumulus cells in cumulus-oocyte complexes normally do not produce uPA. However, cumulus cells stripped from oocytes and stimulated by FSH secrete uPA. uPA secretion is greatly reduced by culturing the cumulus cells with oocytes or oocyte conditioned media.

As also demonstrated in the exemplification, recombinant mGDF-9, an oocyte-specific TGF-$\beta$ family growth factor, can induce expression of HAS2 and/or progesterone, and/or inhibit uPA expression in granulosa cells. This effect on HAS2 expression is specific to GDF-9 as predicted by the follicle culture experiments and not induced by other oocyte-specific TGF-$\beta$ family members, (i.e., BMP-15 and BMP-6).

As described in Example 3, mouse GDF-9 protein is expressed in all oocytes beginning at the type 3a follicle stage including antral follicles. To explore the biological functions of GDF-9 in the later stages of folliculogenesis including cumulus expansion, mature, glycosylated, recombinant mouse GDF-9 was produced using a Chinese hamster ovary cell expression system. A granulosa cell culture system was established to determine the role of GDF-9 in the regulation of several key ovarian gene products using semi-quantitative RT-PCR. It was found that recombinant GDF-9 induced hyaluronan synthase 2 (HAS2), cyclooxygenase 2 (COX-2), and steroidogenic acute regulator protein (StAR) mRNA synthesis but suppressed urokinase plasminogen activator (uPA) and luteinizing hormone receptor (LHR) mRNA synthesis. Consistent with the induction of StAR mRNA by GDF-9, recombinant GDF-9 increased granulosa cell progesterone synthesis in the absence of FSH. Since induction of HAS2 and suppression of the protease uPA in cumulus cells are key events in the production of the hyaluronic acid-rich extracellular matrix which is produced during cumulus expansion, whether GDF-9 could mimic this process was determined. Using oocytectomized cumulus cell-oocyte complexes, it was shown that recombinant GDF-9 induces cumulus expansion in vitro. These studies demonstrate that GDF-9 can bind to receptors on granulosa cells to regulate the expression of a number of gene products. Thus, besides playing a critical function as a growth and differentiation factor during early folliculogenesis, GDF-9 functions as an oocyte-secreted paracrine factor to regulate several key granulosa cell enzymes involved in cumulus expansion and maintenance of an optimal oocyte micro environment, processes which are essential for normal ovulation, fertilization, and female reproduction.

As described in Example 4, the molecular defects that result due to the absence of GDF-9 were analyzed. The major findings were as follows: 1) There are no detectable signals around GDF-9-deficient follicles for several theca cell layer markers (i.e., 17α hydroxylase, luteinizing hormone receptor (LHR), and c-kit, the receptor for kit ligand). This demonstrates that in the absence of GDF-9, the follicles are incompetent to emit a signal that recruits theca cell precursors to surround the follicle. 2) The primary follicles of GDF-9-deficient mice demonstrate an upregulation of kit ligand and inhibin α. This indicates that it is likely that these two important secreted growth factors, expressed in the granulosa cells, are directly regulated in a paracrine fashion by GDF-9. It is also likely that upregulation of kit ligand, via signaling through c-kit on the oocyte, is directly involved in the increased size of GDF-9-deficient oocytes and the eventual demise of the oocyte. 3) After loss of the oocyte, the cells of the GDF-9-deficient follicles remain in a steroidogenic cluster which histologically resembles small corpora lutea. However, at the molecular level, these cells are positive for both luteal markers (e.g., LHR and P-450 side chain cleavage) and non-luteal markers (e.g., inhibin α and P-450 aromatase). This demonstrates that initially the presence of the oocyte prevents the expression of luteinized markers, but that the absence of GDF-9 at an early time point alters the differentiation program of the granulosa cells. 4) As demonstrated by staining with either PCNA or Ki-67 and TUNEL labeling, the granulosa cells of GDF-9-deficient type 3b primary follicles fail to proliferate but also fail to undergo cell death. This indicates that granulosa cells of type 3b follicles require GDF-9 for continued growth and also to become competent to undergo apoptosis, likely through a differentiation event.

The present invention is illustrated by the following examples which are not intended to be limiting in any way.

EXEMPLIFICATION

Example 1

Granulosa Cell Culture In Vitro Assay for GDF-9 Function

Protocol 21-day old CD-1 mice were obtained either from Charles River Laboratories or from the Baylor College of Medicine barrier facility colony. Each female was primed with 7.5 IU pregnant mare serum gonadotropin (PMSG) (0.3 cc of our stock). Initially 44–48 hours later (42–46 hrs later in the last experiment in Example 1) the mice were sacrificed by cervical dislocation and ovaries collected removing all fat and bursal tissue possible. Ovaries were placed in pre-warmed collection media (DMEM/F12 w/1×GPS and 0.3% BSA) in 30 mm dishes. Under the dissecting scope, granulosa cells were released from large antral follicles by repeated puncturing with a 27½ gauge needle. Clumps of granulosa cells were dispersed by mouth pipetting up and down through a pulled Pasteur pipette. Oocytes and cumulus-oocyte complexes (COC) were separated from the granulosa cells manually. Once all obvious oocytes and COC's were removed, granulosa cells were transferred into a clean dish with more prewarmed collection media, and remaining oocytes and COC were removed. Contents of the second dish were transferred into two 1.5 ml eppendorf tubes and spun 3 minutes at 1500 rpm. Fresh collection media was used to wash remaining cells off the plate and placed into the eppendorfs and spun again at 1500 rpm.

Granulosa cells were resuspended by gentle pipetting in 1×Follicle Culture Medium (alpha MEM, 1×Insulin/Transferrin/Selenite, 1×Glutamine/Penicillin/Streptomycin, 4 ng/ml ovine FSH, +/−10% Fetal Calf Serum) 250 µl–500 µl per ovary collected; 250 µl of granulosa cells were plated per well of a 24 well plate. To each well, 250 µl more 1×follicle culture medium with a 2× amount of the treatment to be studied. Final culture volume was 500 µl.

Experiment 1

Medias:
1) CHO control (conc.)=100 µl concentrated media from CHO A2 (CHO cells carrying no expression vector)+400 µl 1×follicle culture medium (F.C.M.) Final dilution= 1:10.
2) mGDF-9 (concentrated)=50 µl concentrated CHO 19A12 media from mGDF-9 expressing cells+450 1×F.C.M. Final dilution=1:20. Estimated final mGDF-9 concentration=50 ng/ml.
3) mBMP-15 (concentrated)=100 µl concentrated CHO 21 A5 media from mBMP-15 expressing cells+400 µl 1×F.C.M. Estimated final mBMP-15 concentration≧100 ng/ml.
4) mGDF-9+mBMP-15 (concentrated)=50 µl concentrated CHO 19A12 media+100 µl concentrated CHO 21A5 media+350 µl F.C.M.—Estimated final mGDF-9 concentration=50 ng/ml.
*remaining 500 µl of 1×F.C.M.+cells were spun down 3 min. at 1500 rpm, resuspended in 2×F.C.M. 250 µl were plated in two remaining wells.
5) *mGDF-9 (not concentrated)=250 µl CHO 19A12 not concentrated+250 µl 2×F.C.M. with granulosa cells. Estimated final mGDF-9 concentration=300 ng/ml.
6) *mDimer (not concentrated)=250 µl CHO 27A11 not concentrated (CHO cells expressing both mGDF-9 and mBMP-15). Estimated final mGDF-9 concentration<150 ng/ml. Estimated final mBMP-15 concentration>150 ng/ml.

All cells were cultured overnight (~20 hrs) at 37° C. at 5% $CO_2$.

Media was aspirated and 500 µl of RNA Stat-60 (Leedo Medical Supply) was added to each well singly and pipetted up and down to lyse cells. All cells were lysed as verified using the dissecting microscope. To homogenize the cells, cells were pipetted up and down using a P200 pipetman. 100 µl of chloroform was added to each tube, vortexed, then incubated on ice 10 min. The tubes were spun at full speed for 20 minutes at 4° C. The aqueous phase was carefully collected and RNA was precipitated with 250 µl isopropanol at −20° C. for 2 hours. A very small RNA pellet was observed after spinning 30 minutes at full speed at 4° C. The pellet was washed in 70% ethanol and air dried, then resuspended in 100 µl DEPC water and stored at −80° C. cDNA was synthesized from 5 µl of each RNA sample (½ of total recovered) by reverse transcription (RT) using the GIBCO Superscript II reverse transcriptase kit and an oligo-dT primer. Total reaction volume was 20 µl. HAS2 was detected by PCR using the following primers: HAS2-1F (5')=GCTTGACCCTGCCTCATCTGTGG (SEQ ID NO: 1) and HAS2-1R (3')=CTGGTTCAGCCATCTCAGATATT (SEQ ID NO: 2) yielding an expected product of 403 bp from spliced mRNA. GAPDH was used as the control for RNA integrity and detected with the following primer: GAPDH-1F (5')=CATGTTTGTGATGGGTGTGAACC (SEQ ID NO: 3) and GAPDH-1R (3')=TGGGAGTTGCTGTTGAAGTCGCA (SEQ ID NO: 4) yielding a product of 486 bp. 2 µl of each RT reaction was used in a standard 50 µl PCR reaction for each primer set with the following amplification conditions: 3 minutes 94° C., 28×(1 minute 94° C., 30 seconds 60° C., 1 minute 72° C., and 7 minutes at 72° C.). Products were run on a 1.5% agarose gel and visualized.

Results:

Expression of HAS2 was significantly elevated (~10 fold) in samples containing mGDF-9 compared to CHO control and all other growth factors tested.

Experiments 2 & 3

This experiment was repeated two additional times looking at HAS2 induction at 5 hours and >20 hrs in culture with control, mGDF-9, and mBMP-15 medias and have consistently seen that expression of HAS2 is elevated in mGDF-9 treated mural granulosa cells. Additionally, this effect of mGDF-9 is not dependent on the presence of serum in the media or on PMSG stimulation of follicle growth in vivo.

Experiment 4 mGDF-9 and hGDF-9 in both the nonconcentrated and concentrated conditioned media were determined by Western blot. MGDF-9 (conc.) media contained ~1 µg/ml and mGDF-9 nonconcentrated media contained ~0.6 µg/ml. The hGDF-9 conditioned media contained ~1 µg/ml. The following experiment was done using the nonconcentrated mGDF-9 media diluted to the final concentrations of 10 ng/ml, 50 ng/ml, 100 ng/ml. hGDF-9 conditioned media was tested at 50 ng/ml, 100 ng/ml and 300 ng/ml. The purpose was to define an active concentration range and an early timecourse for effect.

Protocol

The protocol followed for this experiment is the same as described above with the following modifications.

The 1×follicle culture media did not contain fetal calf serum, so all effects seen are serum independent.

To increase the size of the precipitated RNA pellet and enhance reliability of the precipitation step 10–20 ng of yeast tRNA was added to each sample during the homogenization step.

The internal control for RNA integrity and quantity was changed to HPRT using the following primers: HPRT-1F (5')=CCTGGTTAAGCAGTACAGCC (SEQ ID NO: 5) and HPRT-2R (3')=TACTAGGCAGATGGCCACAG (SEQ ID NO: 6).

Urokinase plasminogen activator (uPA) levels were examined in each sample as well as HAS2 using the following primers: uPA-3F (5')=GTTCAGAC- TGTGAGAT-CACTGG (SEQ ID NO: 7) uPA-4R (3')=CAGAGAGGACGGTCAGCATGG (SEQ ID NO: 8).

To increase the sensitivity of product detection 0.1 µl of $\alpha P^{32}$-dCTP was added to each PCR reaction. Only 1 µl of RT reaction was used as template and amplification occurred for 20 cycles. 5 µl of each reaction was run on a 4% polyacrylamide gel, the gel was dried and exposed to Kodak X-OMAT autoradiography film.

Results

By 3 hours in culture 100 ng/ml mGDF-9 stimulates HAS2 production and inhibits uPA production compared to the CHO control, whereas 100 ng/ml of hGDF-9 fails to stimulate HAS2 and significantly induces uPA. After 5 hours in culture 10 ng/ml of mGDF-9 induces HAS2, while 50 ng/ml and 100 ng/ml both induce an approximately 5–10 fold higher level. After 5 hours in culture 100 ng/ml of hGDF-9 induces a detectable HAS2 signal, while 300 ng/ml induce a level approaching that of 50 ng/ml of mGDF-9. At 5 hours 100 ng/ml mGDF-9 inhibits uPA expression, while all concentrations of hGDF-9 appear to have a stimulatory effect. These results suggest that the maximum activity of mGDF-9 for inducing HAS2 is around 50 ng/ml, and that hGDF-9 can also bind the mouse GDF-9 receptor to stimulate HAS2 expression, but may be less potent in this in vitro model system. uPA is inhibited by high concentrations of mGDF-9 (at least about 100 ng/ml), but may be stimulated by low concentrations (at most about 50 ng/ml). These observations suggest that GDF-9 regulation of uPA may be dependent on a GDF-9 concentration gradient in the antral cavity generated by diffusion of GDF-9 from the oocyte, with lowest levels reaching the mural granulosa cells which are the furthest from the oocyte, defining where follicle wall breakdown for ovulation will occur.

Conclusions

Taken together these results show that mGDF-9 is the oocyte-derived growth factor that normally causes hyaluronic acid production and inhibition of uPA in the cumulus cells. Additionally, these results indicate that granulosa cells can respond to GDF-9 and express the GDF-9 receptor. See the Table.

TABLE 1

In Vitro Granulosa Cell culture: Summary

| Media | HAS2 (compared to T = 0) | uPA (compared to T = 0) |
|---|---|---|
| CHO control | No Change | + |
| mGDF-9 (10 ng/ml) | + | ++ |
| mGDF-9 (50 ng/ml) | +++ | No Change |
| mGDF (100 ng/ml) | +++ | − |
| hGDF-9 (50 ng/ml) | No Change | +++ |
| hGDF-9 (100 ng/ml) | + | +++ |
| hGDF-9 (300 ng/ml) | ++ | +++ |
| mGDF-9 (50 ng/ml) + mBMP-15 (100 ng/ml) | ++ | Not Determined |

TABLE 1-continued

In Vitro Granulosa Cell culture: Summary

| Media | HAS2 (compared to T = 0) | uPA (compared to T = 0) |
|---|---|---|
| Dimer (mGDF-9 < 150 ng/ml; mBMP15 > 150 ng/ml) | ++ | Not Determined |
| BMP-6 (200 ng/ml) | No Change | Not Determined |

Example 2

Identification of a Stimulatory Effect of Recombinant mGDF-9 on Progesterone Synthesis by In Vitro Cultured Mural Granulosa Cells Protocol Primary granulosa cells were isolated as described above and cultured for 5 or 24 hours with various concentrations of recombinant mGDF-9 in αMEM based media containing 2–5 ng/ml of FSH with or without 10% fetal calf serum as indicated. After culture the media was removed and contaminating non-adherent cells were eliminated by centrifugation. The media was frozen at −20° C. The progesterone level in the media was quantitated by radioimmunoassay (RIA). Briefly, a standard amount of radiolabeled progesterone competes with progesterone contained in the experimental sample for a-progesterone antibody binding sites contained in the RIA tubes. Standards provided allow construction of a standard curve which correlates number of counts bound with progesterone levels in the experimental sample. The progesterone RIA kit was obtained from Diagnostic Products Corporation and detects progesterone levels from 0.1–40 ng/ml using a 100 μl sample volume. Higher concentrations can be measured by diluting the experimental sample before assaying with the provided dilution solution.

Results

Figure 2:
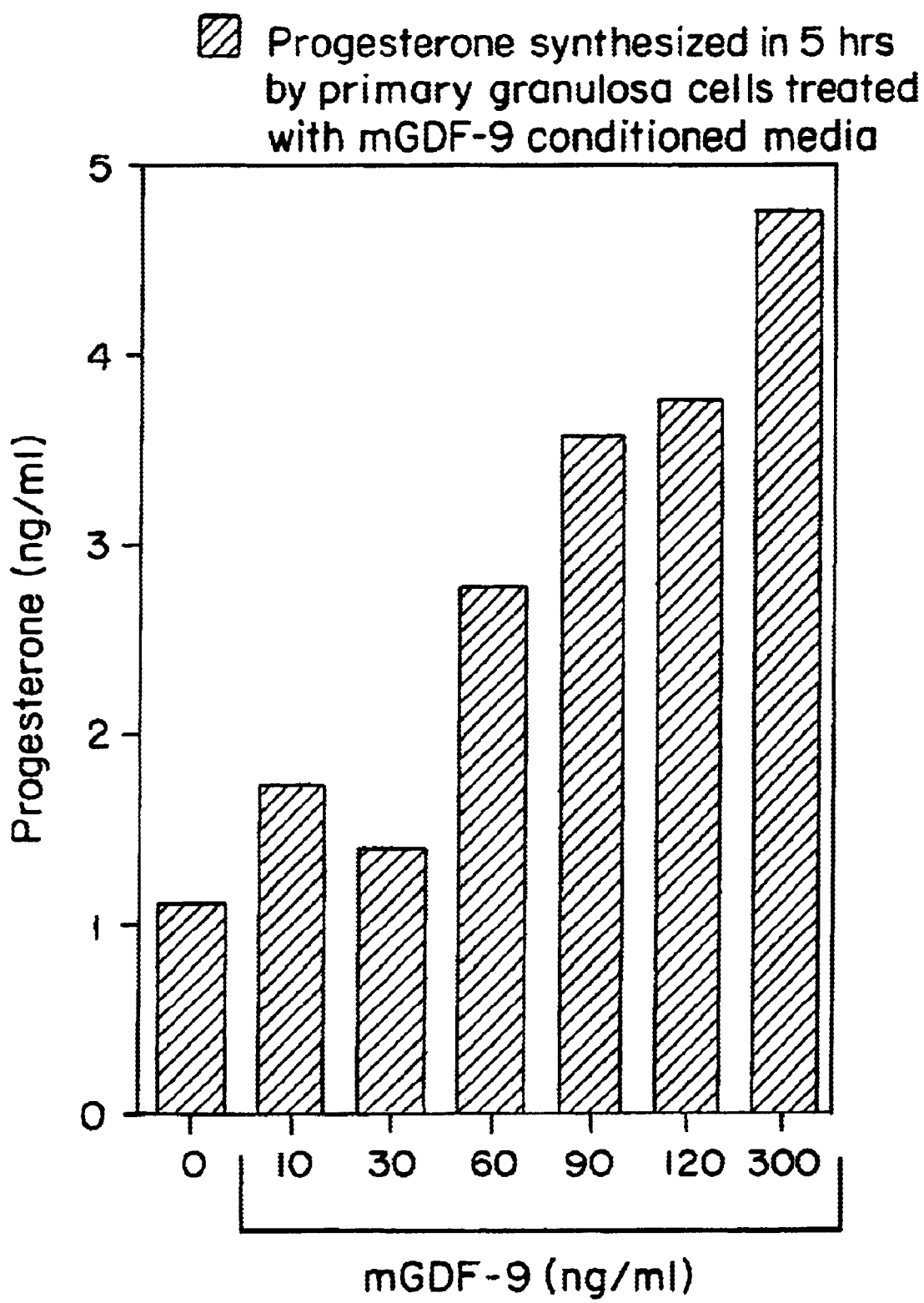
FIG. 2 is a bar graph of the results of a progesterone radioimmunoassay showing that recombinant mGDF-9 stimulated progesterone synthesis by primary granulosa cells in vitro.
Figure 3:
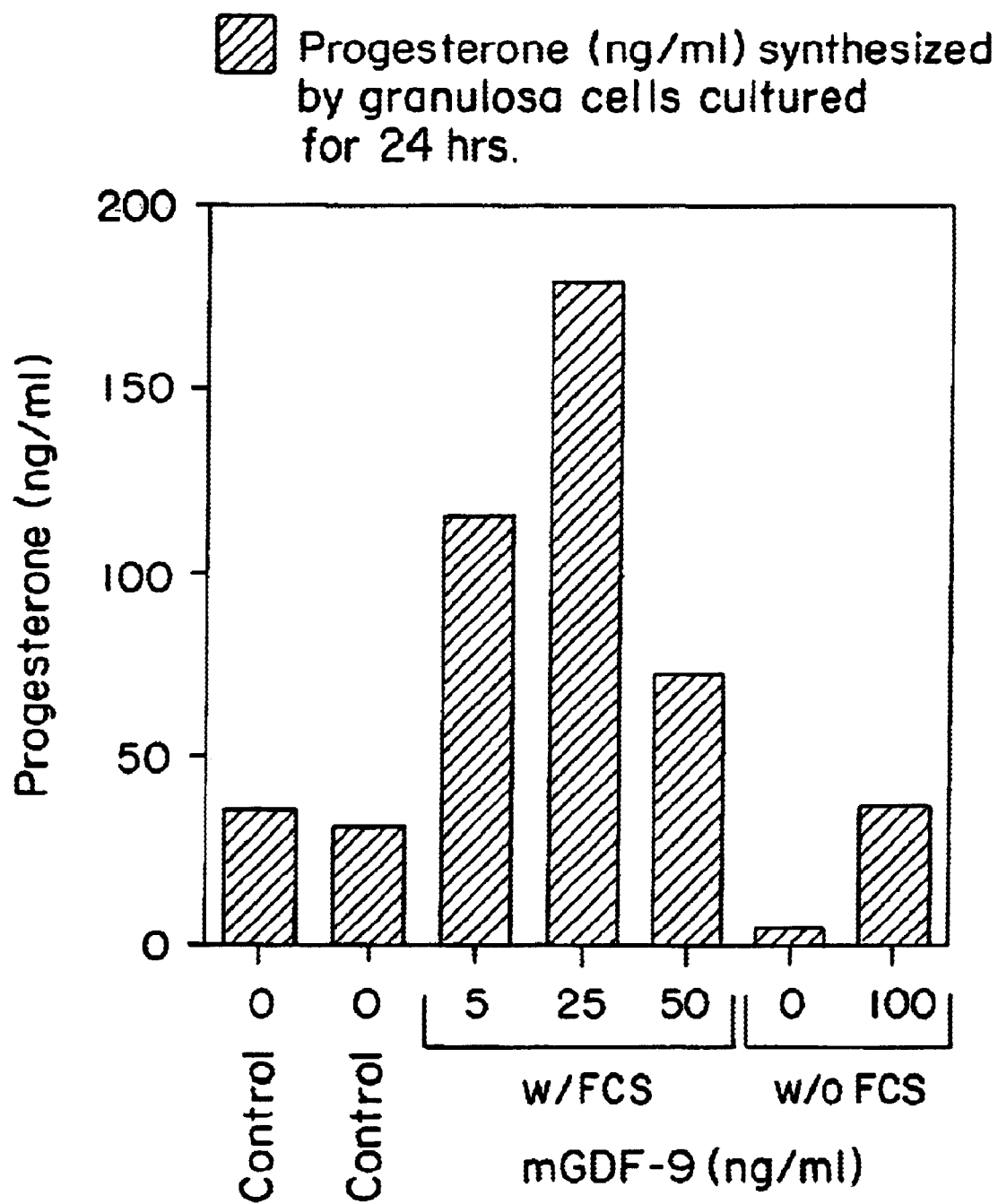
FIG. 3 is a bar graph of the results of a progesterone radioimmunoassay showing that recombinant mGDF-9 with and without fetal calf serum (FCS) stimulated progesterone synthesis by primary granulosa cells in vitro for 24 hours.

Recombinant mGDF-9 stimulated progesterone synthesis by in vitro cultured primary granulosa cells in a time and concentration dependent manner (See FIGS. 1, 2 and 3). At 5 hours, 60 ng/ml of mGDF-9 showed a 2.5 fold increase and 300 ng/ml showed a 4.5 fold increase (see FIG. 2). This stimulation of progesterone is also seen at 24 hours where a 3.5 to 4 fold stimulation was observed (See FIG. 3).

Discussion

The rate limiting step in progesterone synthesis is the catalysis of cholesterol to pregnenolone by the enzyme complex cytochrome P450 side chain cleavage (scc). Non-luteinized cultured rat granulosa cells can be stimulated to increase P450scc MRNA levels and to produce progesterone with forskolin, a cAMP agonist, in vitro (Oonk et al., *J. Biol. Chem.*, 264:21934–21942) indicating that progesterone synthesis at this stage is cAMP-dependent and is associated with increases in P450scc transcription. The results described herein show another function of GDF-9 (i.e., stimulation of progesterone synthesis) and another downstream target gene of GDF-9 signaling (i.e., the cytochrome P450 side chain cleavage gene). Additionally, the measurement of progesterone provides a rapid and easy functional assay for GDF-9 function for the testing of GDF-9 analogs and inhibitors.

Example 3

Paracrine Actions of Growth Differentiation Factor-9 in the Mammalian Ovary

Materials and Methods

Immunohistochemistry.

Ovaries from CD 1 (ICR) mice (generated at Baylor College of Medicine from a Charles River Laboratories stock) were fixed in 10% neutral buffered formalin, processed, and embedded in paraffin. 4 μm ovarian sections were dewaxed then re-hydrated in a graded series of ethanol solutions. Nonspecific binding was reduced by preincubation for 30 minutes in 1×universal blocking buffer (Biogenex, San Ramon, Calif.) diluted in 0.1 M phosphate buffered saline (PBS) and 0.1% BSA. The primary antibody, mouse anti-human GDF-9 monoclonal antibody, was supplied by Dr. Neil Wolfman (Genetics Institute, Cambridge, Mass.) and was added to each section and incubated for 2 hours at a final concentration of 30–60 ng/μl. Sections were washed twice in 0.1% BSA in PBS for 5 minutes followed by incubation for 20 minutes in biotinylated goat anti-mouse IgG (Biogenex, San Ramon, Calif.). Following washing as above, the sections were incubated for 20 minutes in alkaline phosphatase conjugated streptavidin (Biogenex, San Ramon, Calif.), washed twice in 0.1% BSA in PBS and incubated with New Fuchsin alkaline phosphatase substrate as per manufacturer's instructions (Biogenex). After detection of a positive reaction, sections were counter-stained with hematoxylin and mounted in glycerol.

Production of Recombinant Mouse GDF-9.

A full length mouse GDF-9 cDNA (Incerti, B., et al., *Biochim. Biophys. Acta.*, 1222:125–128 (1994)) was subcloned into the expression vector pHTop containing the processing gene PACE (a gift from Dr. Monique Davies, Genetics Institute, Cambridge, Mass.). The GDF-9 expression vector was lipofectin transfected into CHO cells under standard conditions (Gibco BRL Life Technologies). Expression of mouse GDF-9 in CHO cells was subsequently driven by a tet-regulatable promoter while an SV40 promoter regulated expression of PACE. Stable, positive clones were selected in the presence of 0.02 μM methotrexate in α-modified eagles' medium (αMEM) containing 10% heat inactivated dialyzed fetal bovine serum, 100 μg/ml G418-sulfate (Gibco BRL Life Technologies) and the antibiotics gentamicin, penicillin, and streptomycin. Following clonal selection and expansion in 0.02 μM methotrexate, the GDF-9-expressing cells were incubated for 24 hours in Opti-MEM reduced serum collection media containing 100 mg/ml heparin (SIGMA, St. Louis, Mo.). The media were harvested, and GDF-9 protein levels were determined by SDS-polyacrylamide gel electrophoresis (PAGE) with subsequent immunoblotting (see next section).

Western Blot Analysis.

Samples of GDF-9-containing media were electrophoresed on a 5% stacking/15% resolving SDS polyacrylamide gel in a Biorad Mini-Subcell apparatus as previously described (Sambrook, J., et al., "In: Molecular Cloning": *A Laboratory manual*, (N. Ford and C. Nolan, eds) Vol. 3, 2nd Ed., 3 vol., Cold Spring Harbor Laboratory Press, Cold Spring Harbor, USA (1989)) and subsequently transferred to PVDF membrane. The membranes were blocked overnight in a 5% nonfat milk in 1×Tris-buffered-saline with 0.05% Tween-20. Mouse antihuman GDF-9 monoclonal antibody (described above) was used at a 1:1000 dilution in blocking solution, and an anti-mouse secondary antibody conjugated to horseradish peroxidase (Southern Biotechnology Associates, Birmingham, Ala.) was used at a 1:2500 dilution in blocking solution. Chemiluminescence using ECL western detection reagents (Pierce, Rockford, Ill.) and autoradiographic film detected signal. Bands were quantitated using a densitometer (Molecular Dynamics) and Imagequant software, and the concentration of GDF-9 in the conditioned media was determined by comparing the signal intensity of GDF-9 in the conditioned media to known concentrations of GDF-9 standards run concurrently. Several batches of recombinant mouse GDF-9 were produced during the course of these studies, all of which appeared to have similar activities based on Western blot quantitation (i.e., immunoreactivity correlated with bioactivity).

Isolation and Culture of Granulosa Cells.

21–24 day-old female CD-1 (ICR) mice (Baylor College of Medicine) were injected with 7.5 IU Gestyl (Diosynth, B. V., Holland) and ovaries were harvested 44–48 hours later, dissected free of fat and surrounding tissue, and placed in minimal essential media with 25 mM HEPES supplemented with 0.3 mg/ml L-glutamine, 100 U/ml penicillin, 0.1 mg/ml streptomycin (Gibco BRL, Grand Island, N.Y.), and 0.3% BSA (SIGMA).

Mural Granulosa Cells Were Released by Puncturing Large Antral Follicles.

Oocytes and cumulus cell-oocyte complexes (COC's) were carefully removed (see below), Granulosa cells from multiple ovaries were pooled, centrifuged, and resuspended in 2×granulosa cell culture media (GCM): αMEM (GibcoBRL) with 0.6 mg/ml L-glutamine, 200 U/ml penicillin, 0.2 mg/ml streptomycin, and 2×insulin-transferring-selenite (GibcoBRL) in the presence or absence of 20% fetal bovine serum (Hyclone Laboratories, Logan, Utah), and the presence or absence of ovine FSH (NIDDK-o-FSH-20 kindly provided by Dr. Parlow of the National Hormone and Pituitary Program). GDF-9-containing media or control conditioned media were diluted to 2× the final concentration in α-MEM. Equal volumes of 2×GDF-9-containing media or control media were combined with granulosa cells in 2×culture media and cultured at 37° C. in a humidified atmosphere with 5% $CO_2$. After varying periods of culture, non-adherent cells were pelleted from the media, and the media were stored at −20° C. Granulosa cells were lysed and total RNA was isolated using RNA Stat-60 (Leedo Medical Laboratories, Houston, Tex.) following manufacturer's protocol.

Semi-quantitative RT-PCR Analysis.

Oligo-dT primed cDNA from each RNA sample was synthesized using Superscript reverse transcriptase (GibcoBRL) following the manufacturer's protocol. 1 µl of each RT reaction (1/20 of total) was used in each 25 µl PCR reaction primed with gene-specific oligonucleotides. Mouse HAS2 mRNA expression was detected using 5' GCTTGAC-CCTGCCTCATCTGTGG 3' (SEQ ID NO: 1) (sense) and 5' CTGGTTCAGCCATCTCAGATATT 3' (SEQ ID NO: 2) (antisense) primers (Fulop, C., et al., *Arch. Biochem. Biophys.*, 337:261–266 (1997)) which span a 1.4 kb intron. A PCR product of 403 bp is amplified from RNA, easily distinguished from amplification of contaminating DNA. Mouse uPA mRNA expression was detected using 5' GTTCAGACTGTGAGATCACTGG 3' (SEQ ID NO: 7) (sense) and 5' CAGAGAGGACGGTCAGCATGG 3' (SEQ ID NO: 8) (antisense) primers that span two introns of 1.4 kb total length. A PCR product of 434 bp is amplified from RNA. Mouse hypoxanthine phosphoribosyltransferase (HPRT) was amplified using 5' CCTGGTTAAGCAGTA-CAGCC 3' (SEQ ID NO: 5) (sense) and 5'TACTAGGCA-GATGGCCACAG 3' (SEQ ID NO: 6) (antisense) primers which span three introns of unknown sizes and gives an expected mRNA-derived product size of 309 bp from RNA. Mouse StAR mRNA expression was detected using 5' TCGCTTGGAGGTGGTGGTAGAC 3' (SEQ ID NO: 9) (sense) and 5' GCAGGTCAATGTGGTGGACAGT 3' (SEQ ID NO: 10) (antisense) primers which span multiple small introns and give an mRNA-derived 522 bp product. Mouse cholesterol side chain cleavage P-450 mRNA expression was detected using 5' GCCAACATTACCGAGATGC 3' (SEQ ID NO: 11) (sense) and 5' CGAACACCCCAGC-CAAAGCC 3' (SEQ ID NO: 12) (antisense) primers and give an mRNA-derived 426 bp product. Mouse COX-2 mRNA expression was detected using 5' CTC-CTTTTCAACCAGCAGTTCC 3' (SEQ ID NO: 13) (sense) and 5' TCTGCAGCCATTTCCTTCTCTC 3' (SEQ ID NO: 14) (antisense) primers and give a 377 bp product. Mouse LH receptor mRNA expression was detected using 5' CTTATACATAACCACCATACCAG 3' (SEQ ID NO: 15) (sense) and 5' ATCCCAGCCACTGAGTTCATTC 3' (SEQ ID NO: 16) (antisense) primers which span multiple introns and give a 516 bp product. PCR products amplified from granulosa cell cDNA were initially isolated, subcloned, and sequenced to confirm that they matched published sequences. In later studies, $[\alpha^{32}P]$-dCTP was added to each PCR reaction and products were separated by electrophoresis on a 4% polyacrylamide gel. The gels were dried and exposed to autoradiography, and radioactive bands quantitated on a Molecular Dynamics phosphorimager (Storm 860).

Northern Blot Analysis.

Total RNA was isolated from granulosa cells and quantitated by fluorometry using Ribogreen RNA quantitation reagents (Molecular Probes, Eugene, Oreg.) on a VersaFluor fluorometer (BIORAD, Hercules, Calif.) using a 485–495 nm excitation filter and 515–525 nm emission filter. 15 µg of total RNA of each sample were electrophoresed on a 1.2% agarose/7.6% formaldehyde gel and transferred to Hybond N nylon membrane (Amersham, Arlington Heights, Ill.). Probes for HAS2 and uPA were generated from the aforementioned subcloned PCR products by random priming with $[\alpha^{32}P]$-dATP using the StripEZ probe synthesis kit (Ambion, Austin, Tex.). The membrane was hybridized, washed, and subjected to autoradiography as described (Mahmoudi, M. and Lin, V. K., *Biotech.*, 7:331–332 (1989)). The probe was removed from the membrane using the Strip-EZ removal reagents (Ambion) following the manufacturer's protocol. The same blots were then reprobed with glyceraldehyde-3-phosphate dehydrogenase (GAPDH) as a loading control. Signals for each probe were quantitated on a Molecular Dynamics phosphorimager.

Progesterone Radioimmunoassay.

Progesterone in the culture media was measured in duplicate by a specific, solid-phase radioimmunoassay using a kit from Diagnostic Products Corporation (Los Angeles, Calif.) according to the manufacturer's instructions. The sensitivity of this assay is 0.02 ng/ml, and calibration standards between 0. 1 and 40 ng/ml were used.

Expansion of Oocytectomized Complexes.

Cumulus cell-oocyte complexes were collected as described above. The oocyte was removed from each complex using a micro injection apparatus as previously described (Buccione, R., et al., *Dev. Biol.*, 138:16–25 (1990)). Successful oocytectomy was assessed by the removal of the germinal vesicle along with the majority of ooplasm. Oocytectomized complexes were incubated for 18 hours in groups in 20 µl droplets of granulosa cell culture media supplemented with 10% fetal bovine serum and 5 ng/ml or 100 ng/ml of oFSH with or without 1 µg/ml oLH in the presence or absence of 100 ng/ml GDF-9 . Photographs were taken on a Nikon inverted microscope.

Results

Immunohistochemical Detection of GDF-9 in Mouse Ovaries.

Using a monoclonal antibody to human GDF-9, GDF-9 protein was specifically detected in mouse oocytes. At low power magnification of an immunohistochemically-stained ovary, GDF-9 immunoreactivity was detected only in oocytes, whereas oocytes in GDF-9-deficient ovaries did not stain. Primordial (type 2) oocytes were negative consistent with the absence of GDF-9 mRNA expression (McGrath, S. A. et al., *Mol. Endocr.*, 9:131–136 (1995)) and Elvin and Matzuk, unpublished data). GDF-9 immunoreactivity was first seen at low (and variable) levels in oocytes of type 3a follicles (follicles with less than 20 cuboidal granulosa cells arranged in one concentric layer around the oocyte) and was higher in the oocytes of type 3b follicles and beyond. Full-grown oocytes of multilayer preantral follicles consistently stained more intensely for GDF-9, and GDF-9 immunoreactivity was clearly detected in oocytes of cumulus cell-oocyte complexes of large antral and pre-ovulatory follicles. As expected for a secreted peptide, GDF-9 immunoreactivity was excluded from the germinal vesicle (i.e., nucleus). Interestingly, an asymmetric staining pattern was frequently observed within the oocytes likely due to the detection of the precursor forms of GDF-9 within the oocyte endoplasmic reticulum and Golgi complex (Wasserman, P. M. and Albertini, D. F., "The mammalian ovum", *In: E. Knobil and J. Neill* (ed) *The physiology of reproduction*, Raven Press, New York, pp. 79–122 (1994)). Thus, GDF-9 mRNA and protein are synthesized by oocytes of all growing follicles suggesting that it could function at all stages of folliculogenesis.

Production of Recombinant Mouse GDF-9.

To study the function of GDF-9 at later stages of folliculogenesis, it was necessary to produce recombinant GDF-9. Chinese hamster ovary (CHO) cells were stably transfected with an expression vector containing both a full-length mouse GDF-9 cDNA and a cDNA for PACE, a prepropeptide sequence cleaving enzyme. Western blot analysis of medium from CHO cells containing the mouse GDF-9 expression vector, analyzed under denaturing conditions, demonstrated two unique bands of approximate molecular weights 21 kD and 60 kD which were not present in mock conditioned medium. Proteolytic processing of GDF-9 at its tetrabasic R-R-R-R site would be predicted to yield a carboxyl-terminal mature peptide of 135 amino acids with a predicted molecular weight of approximately 15.6 kD (McPherron, A. C. and Lee, S.-J., J. Biol. Chem., 268:3444–3449 (1993)). The mature GDF-9 sequence contains a single N-linked glycosylation site ($Asn^{325}$-$Leu^{326}$-$Ser^{321}$). The predominant 21 kD form would correspond to the cleaved, mature monomeric form of mouse GDF-9 with one N-linked oligosaccharide. This band ran at an identical position as the recombinant human GDF-9 synthesized in CHO cells. The band at 60 kD corresponded to the glycosylated, unprocessed (prohormone) form (441 amino acids) which is also secreted into the media. To confirm that the increased molecular weight of these two forms was due to N-linked glycosylation, GDF-9-containing medium was treated with N-glycanase to remove the N-linked oligosaccharides. This treatment reduced the size of the 21 kD band to 16 kd, the same molecular weight as the bacterially-produced GDF-9 mature peptide, and also reduced the 60 kD band to 50 kD. Since the 21 kD glycosylated GDF-9 form is always the most abundant form, this strategy to produce recombinant, glycosylated GDF-9 in mammalian cells in the presence of PACE and under serum free culture conditions is efficient.

Regulation of Hyaluronan Synthase 2 (HAS2) and uPA mRNA Synthesis by Recombinant GDF-9.

Oocytes secrete a growth factor which is known to stimulate hyaluronic acid synthesis, inhibit urokinase plasminogen activator (uPA), and cause cumulus expansion in vitro (Salustri, A., et al., *Zygote*, 4:313–315 (1996)). Hyaluronan synthase 2 (HAS2), which is expressed in mouse cumulus cell-oocyte complexes after the gonadotropin surge and immediately preceding efficient cumulus expansion (Fülop, C., et. al., *Arch. Bioch. Bioph.*, 337:261–266 (1997)), has been implicated as the major hyaluronic acid synthase involved in cumulus expansion (Spicer, A. P. et al., *J. Biol. Chem.*, 271:23400–23406 (1996)). To determine if GDF-9 is the oocyte-secreted factor responsible for inducing cumulus expansion through increased hyaluronic acid matrix synthesis and decreased hyaluronic acid matrix degradation, the expression levels of HAS2 and uPA in freshly isolated granulosa cells treated with recombinant mouse GDF-9 were examined. RT-PCR incorporation of radiolabeled nucleotides into specific products was used to monitor the expression levels of HAS2 and uPA in control and GDF-9-treated granulosa cell cultures. First, a linear range of product amplification for each oligonucleotide pair of the three genes (i.e., HAS2, uPA, and HPRT) was established. Using radiolabeled [$\alpha$-$^{32}$P]-dCTP in the PCR reaction, identical samples were amplified for 16–22 cycles and quantitated using photodensitometric analysis of the autoradiographic film. Linear increases in amplified product were observed for HPRT over 16–20 cycles, for HAS2 over 16–20 cycles, and for uPA over 18–22 cycles from both control and GDF-9-treated samples. 18–20 cycles were determined to be optimal and were used to study all three gene products in all further analysis. Similar PCR conditions were performed for the COX-2, LH receptor, P-450scc, and StAR studies (see below).

Next, the dose-response relationship between recombinant GDF-9 and HAS2 mRNA synthesis was examined. The rate of hyaluronic acid synthesis by cumulus cells or mural granulosa cells exposed to oocyte-conditioned media peaks at 6–12 hours in culture (Salustri, A., et al., *J. Biol. Chem.*, 264:13840–13847 (1989) and D'Alessandris, T. E., et al., *J. Biol. Chem.*, 272:4787–4794 (1997)). Thus, for the dose-response experiment, granulosa cells were cultured for 5 hours in the absence or presence of varying concentrations of recombinant GDF-9. Using semi-quantitative RT-PCR, a small increase in HAS2 expression with 10 ng/ml of recombinant GDF-9 can be detected. Levels of recombinant GDF-9 between 30–300 ng/ml gave robust HAS2 induction with a relatively linear dose/response occurring between 30–120 ng/ml. Granulosa cells collected from unprimed immature mouse ovaries also responded similarly to the recombinant GDF-9. In contrast, recombinant mouse BMP-15 (150 ng/ml) or recombinant human BMP-6 (50 ng/ml) were unable to stimulate HAS2 expression or suppress uPA expression when tested in any of the granulosa cell assays. These findings demonstrate that these activities are specific to GDF-9 and that other oocyte-secreted TGF-$\beta$ family members cannot replicate these activities.

A time-course analysis (0–24 hours) of the HAS2 expression pattern using 100 ng/ml of GDF-9 demonstrated a small induction of HAS2 mRNA at 2 hours, a peak induction between 3–5 hours in culture, and by 9 hours in culture, the HAS2 expression level was decreasing. Granulosa cells cultured in the absence of GDF-9 for 0–24 hours express >10-fold lower levels of HAS2 compared to the GDF-9-induced peak level, indicating a very low level of basal activity in these cells. The time course for uPA expression in control granulosa cells cultured in the absence of GDF-9 indicated that uPA levels increase over the first 9 hours in culture. However, granulosa cells treated with 100 ng/ml of recombinant GDF-9 maintained a detectable but much lower level of uPA expression. At 5 hours, the band intensity from the GDF-9-treated sample was ~15% of the control, and at 9 hours, it was ~9% of the control treated sample band intensity (normalized to HPRT for each sample).

To confirm the effects of GDF-9 on HAS2 and uPA expression as seen by RT-PCR, the expression of HAS2 in primary granulosa cells was examined by Northern blot analysis in the presence or absence of 50 ng/ml of GDF-9 . Total RNA from each sample (at 0 or 5 hours incubation in the presence or absence of 50 ng/ml GDF-9) was subjected to Northern blot analysis and hybridized with either an HAS2 or uPA probe and subsequently with a GAPDH probe. The signals were quantitated on a phosphorimager and HAS2 and uPA levels and normalized to GAPDH. HAS2 was barely detectable in mural granulosa cells at 0 hours or after 5 hours of culture in the control sample. However, after 5 hours incubation with GDF-9, both the 4.8 kb and 3.2 kb HAS2 mRNA forms (Spicer, A. P., et al., *J. Biol. Chem.*, 271:23400–23406 (1996)) were increased 9.7-fold compared to control. In contrast, Northern blot analysis of uPA showed that 50 ng/ml GDF-9 suppressed uPA synthesis to 40% of control cultures. Thus, the Northern blot data confirmed our RT-PCR analyses. Recombinant GDF-9 causes cumulus expansion of oocytectomized cumulus cell-oocyte complexes.

Intact cumulus cell-oocyte complexes were isolated from PMSG-treated immature female mice. Using a transgenic micro manipulator set-up, the oocytes from these complexes were punctured, and the oocyte contents were suctioned. Before culture, these oocytectomized cumulus complexes were spherical objects approximately 100 $\mu$m in diameter consisting of several layers of granulosa cells that surround an empty zona pellucida. After 18 hours in culture, cumulus cells from 25 out of 25 oocytectomized complexes cultured in control media (i.e., deficient in GDF-9 but containing 10% fetal calf serum and 5 ng/ml or 150 ng/ml of FSH) adhered to the tissue culture plate and assumed a fibroblastic appearance. Consistent with previous reports that cumulus cells have low or undetectable levels of LH receptor mRNA, incubation of these oocytectomized complexes (9 out of 9) with LH (1 $\mu$g/ml) failed to alter their fibroblastic appearance. In contrast, 40 out of 44 oocytectomized complexes, isolated under identical conditions and cultured in the presence of 100 ng/ml GDF-9, maintained a spherical appearance, and expanded into a three-dimensional, gelatinous sphere. These results are similar to cumulus cell-oocyte complexes with intact oocytes cultured in FSH-containing media. These cells did not detach from the plate because of cell death since the majority of cells continued to exclude the vital dye, trypan blue. In contrast, incubation of the complexes with recombinant human BMP-6 or BMP-15 did not result in cumulus expansion. These observations indicate that GDF-9 specifically stimulates cumulus expansion and is the oocyte-derived factor that normally mediates this process.

Regulation of LH Receptor and Cyclooxygenase 2 (COX-2) by GDF-9.

Based on the above findings, the effect of recombinant mouse GDF-9 on LH receptor and COX2 expression in granulosa cell cultures was determined using semi-quantitative RT-PCR. After collection of the granulosa cells (T=0), a low level of LH receptor was detected. In the absence of GDF-9, the levels of LH receptor were reduced further but expression increased from 5 hours to 24 hours. In contrast, incubation of the granulosa cells with GDF-9 (100 ng/ml) suppressed LH receptor mRNA synthesis at all time points. Even in the presence of 10 ng/ml FSH, LH receptor mRNA was suppressed in the presence of 100 ng/ml GDF-9. In the experiment shown using 10 ng/ml FSH, the control-treated granulosa cells expressed ~30 fold more LH receptor than the GDF-9-treated granulosa cells ($p<0.05$, n=3). In contrast, COX-2 expression was low in the absence of GDF-9, but demonstrated dramatically elevated levels after 24 hours of incubation in the presence of 100 ng/ml GDF-9. While FSH had no significant effect in either the control or GDF-9-treated granulosa cells, GDF-9 caused a >50-fold increase in COX-2 expression ($p<0.05$, n=6). Analysis of HAS2 expression in these samples was consistent with previous results.

GDF-9 Regulation of Progesterone Synthesis.

Figure 4A:
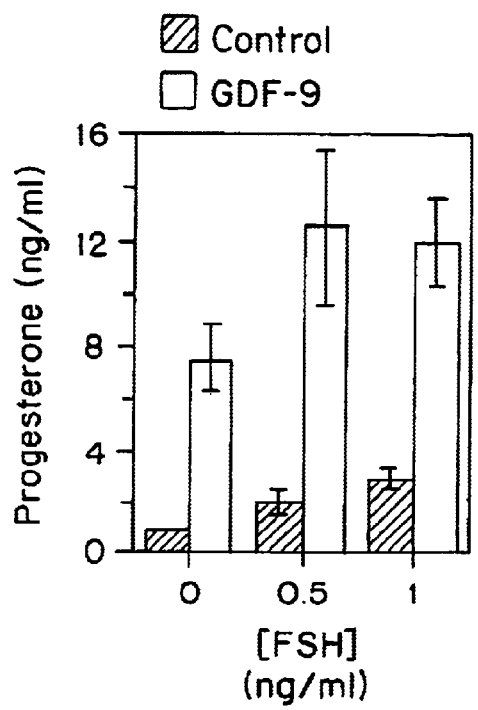
FIG. 4A is a bar graph showing the level of progesterone in the media of granulosa cells cultured for 14 hours in serum-free media in the absence or presence of 50 ng/ml GDF-9 in the presence of varying concentrations of 0, 0.5, or 1 ng/ml FSH; the error bars represent the standard error of the mean (SEM). *, $p<0.05$ for control vs. 50 ng/ml GDF-9 at FSH=0 ng/ml, FSH=0.5 ng/ml, or FSH=1 ng/ml.
Figure 4B:
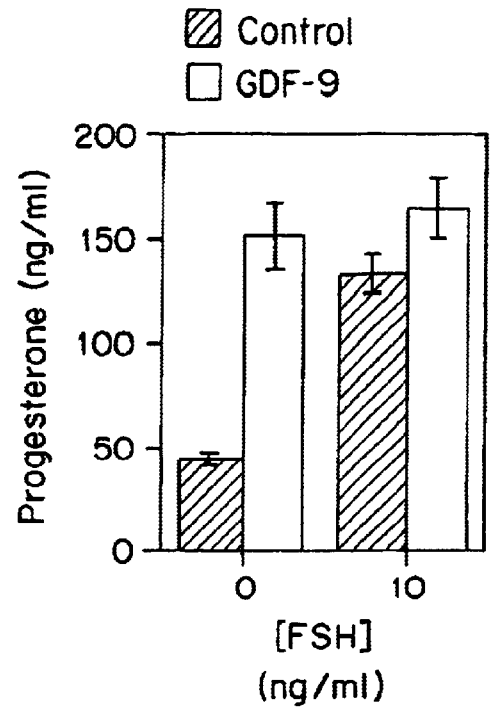
FIG. 4B is a bar graph showing the level of progesterone in the media after 24 hours of treatment of cells +/−GDF-9 (100 ng/ml) or FSH for triplicate samples in 10% of FCS containing media. *, $p<0.05$ for control versus GDF-9-treated cells cultured without FSH.

To study the effects of GDF-9 and FSH on the regulation of progesterone synthesis, dose-response and time course experiments were performed. Semi-quantitative RT-PCR was performed to analyze P-450scc mRNA synthesis and StAR mRNA synthesis and a radioimmunoassay was used to analyze progesterone secreted into the media. Media were collected from granulosa cells cultured in triplicate wells for 4 hours containing varying amounts of FSH in the presence or absence of 50 ng/ml GDF-9 and assayed for progesterone by radioimmunoassay. Under these conditions, granulosa cells cultured for 4 hours in the absence or at low levels of FSH produced very little progesterone, whereas granulosa cells cultured with 50 ng/ml GDF-9 produced 5–7 fold higher amounts of progesterone (FIG. 4A). Granulosa cells were incubated for 24 hours in media containing 10% FCS with 0 or 10 ng/ml FSH in the presence or absence of GDF-9. However, the amount of progesterone produced in the presence of 5 ng/ml FSH was not significantly influenced by the presence or absence of GDF-9 and was ~2–3 fold greater than that produced in the presence of only GDF-9 or at low levels of FSH. After incubation for 24 hours, GDF-9 alone induced significantly higher amounts of progesterone but in the presence of high concentrations of FSH (10 ng/ml), the effect of the GDF-9 was negligible (FIG. 4B). These data indicate that FSH and GDF-9 stimulation of progesterone are not additive.

Figure 4C:
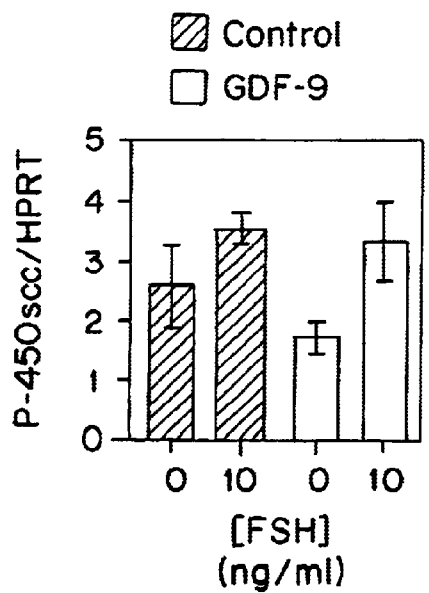
FIGS. 4C–4D are bar graphs showing quantitation of the P-450scc and StAR mRNA levels from the experiment of FIGS. 4A and 4B normalized to HPRT levels; each value is the mean+/−SEM of duplicate or triplicate wells; the control-treated samples (n=4) at FSH=0 or 10 ng/ml in the StAR mRNA analysis.
Figure 4D:
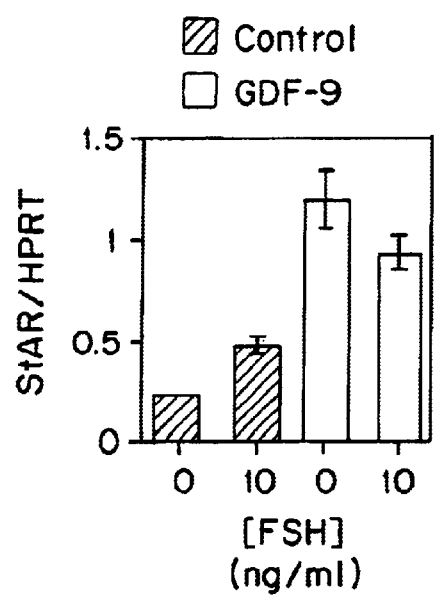

To determine how FSH and GDF-9 regulate progesterone synthesis in the granulosa cell cultures, the levels of P-450scc and StAR mRNA were analyzed by semi-quantitative RT-PCR after incubation for 24 hours in the presence or absence of FSH or the presence or absence of GDF-9 (FIGS. 4C–4D). Whereas 10 ng/ml FSH caused a small increase in P-450scc, the presence of GDF-9 did not have any effect. In contrast, GDF-9 resulted in 2–5 fold induction of the StAR mRNA levels ($p<0.05$). These results suggest that FSH and GDF-9 function to regulate a significant progesterone synthesis via different mechanisms.

Discussion

Using immunohistochemical analysis it is shown herein that GDF-9 protein is first detected at low levels within growing oocytes of primary follicles (type 3a follicles), is present at higher levels in full-grown oocytes of type 3b follicles, and is detected in oocytes of every subsequent developmental stage. In addition, it has been shown that GDF-9 protein is also synthesized by oocytes of large antral and pre-ovulatory follicles in which the oocyte is closely associated with cumulus cells. Although the GDF-9 protein is detected in oocytes of type 3a follicles, it only becomes essential for folliculogenesis at the type 3b-type 4 follicle transition. This indicates that the GDF-9 signal transduction cascade is not active prior to the type 3b follicle stage.

As shown herein, GDF-9 could substitute for oocytes and oocyte-conditioned media in assays analyzing HAS2 induction and uPA suppression typical of processes occurring in pre-ovulatory follicles. As also shown herein, other oocyte-expressed TGF-β family members, BMP-15 and BMP-6, were unable to substitute for GDF-9 in these granulosa cell assays. Mural granulosa cells, isolated from antral follicles treated with recombinant GDF-9, were induced to express HAS2 in a dose-dependent and time dependent manner. GDF-9 induced approximately 10-fold higher levels of HAS2 mRNA in mural granulosa cells which corresponds well to the maximum effect of oocytes on HA synthesis. Additionally, the dose-response curve for GDF-9 was very similar to that of the oocyte-conditioned media. Very low doses (e.g., 0.5 oocytes/μl or 10 ng/ml GDF-9) induced very low but detectable increases in hyaluronic acid synthesis or HAS2 expression whereas 1 oocyte/μl or 30–50 ng/ml GDF-9 caused a much more dramatic induction which plateaus at 2–4 oocytes/μl or 120–300 ng/ml GDF-9 (Salustri, A., et al., *Dev. Biol.*, 138: 26–32 (1990)). The time course of GDF-9 action also agreed with previous data for the oocyte-produced factor. Whereas HAS2 mRNA was induced by 2 hours in culture with GDF-9, oocyte-induced hyaluronic acid became detectable at low levels after 2.5 hours (Salustri, A., et al., *J. Biol. Chem.*, 264:13840–13847 (1989)). GDF-9 induced peak HAS2 mRNA levels between 3–5 hours, while the rate of oocyte-induced hyaluronic acid synthesis was maximal between 6–12 hours (Salustri, A., et al., *J. Biol. Chem.*, 264:13840–13847(1989)). Likewise, oocyte-induced hyaluronic acid synthesis dropped after 12 hours and no more hyaluronic acid was made after 18 hours (D'Alessandris, T. E., et al., *J. Biol. Chem.*, 272:4787–4794 (1997)); GDF-9-induced HAS2 expression was reduced by 24 hours and uPA synthesis increased by 24 hours. It is likely that the "transient" nature of the activation of HAS2 expression and hyaluronic acid synthesis and the increase in uPA synthesis over this time period may be due to lability of GDF-9 in the media, down regulation of the GDF-9 receptor, GDF-9-induced differentiation of the granulosa cells, and/or stimulation of a negative feedback mechanism within the GDF-9 signal transduction cascade. It is interesting to note that the oocyte secreted factor that regulates several of these processes has been noted to be labile and that continued presence of oocytes in various co-cultures with granulosa cells is required for continued activity (Eppig, J. J., et al., *Biol. Reprod.*, 56:976–984 (1997)). Lastly, the data described herein indicates that the difference in the in vivo phenotype of mural granulosa cells versus expanding cumulus granulosa cells is not intrinsic to the cells themselves but is due to their proximity to the oocyte and the concentration gradient of the oocyte-produced GDF-9.

The conversion of cholesterol to pregnenolone is the rate-determining step in granulosa cell steroidogenesis. The rate of pregnenolone synthesis depends on the level and activity of the reaction catalyzing enzyme, cytochrome P-450 side chain cleavage (P-450scc), and its access to its substrate cholesterol via stimulation of the steroidogenic acute regulatory protein (StAR) (Rennert, H., et al., "Intracellular cholesterol dynamics in steroidogenic cells", In: L. C. Adashi, E. Y. (ed) *The Ovary*, Raven Press, Ltd., New York, pp. 1470164 (1993)). It is well established that FSH- and LH-induced increases in intracellular cAMP, leading to subsequent stimulation of P-450scc and StAR mRNA synthesis and StAR protein phosphorylation, stimulate progesterone synthesis in vitro (Richards, J. S. and Hedin, L., *Annu. Rev. Physiol.*, 50:441–463 (1988); Clark, B. J. et al., *Mol. Endocr.*, 9:1346–55 (1995) and Arakane, F., et al., *J. Biol. Chem.*, 272:32656–62 (1997)). In contrast to the effect seen with GDF-9 treatment, activin A decreased basal and FSH stimulated P-450scc, 3β hydroxysteroid dehydrogenase (3βHSD) and progesterone synthesis by cultured granulosa cells from diethylstilbestrol (DES) stimulated rat. The data described herein confirms that FSH stimulates P-450scc mRNA synthesis in mouse granulosa cells but demonstrates that GDF-9 did not significantly affect P-450scc mRNA synthesis. In contrast, FSH has only a small inductive effect on StAR mRNA, but GDF-9 with or without FSH significantly induces StAR expression. Consequently, both GDF-9 and FSH can independently increase production of progesterone by the granulosa cells and appear to function in the same pathway but via different mechanisms. It is likely that this local production of progesterone by the cumulus cells may be critical for achieving a perfect microenvironment for the oocyte after ovulation and prior to fertilization. In support of this, ovulated rat cumulus cell-oocyte complexes secrete measurable levels of both progesterone and prostaglandins (mainly PGE2) (Schuetz, A. W., and Dubin, N. H., *Endocr.*, 108:457–463 (1981)), and use of aminoglutethimide, which inhibits conversion of cholesterol to pregnenolone, reduces the number of normal ovine oocytes recovered after in vitro follicular maturation.

Figure 5:
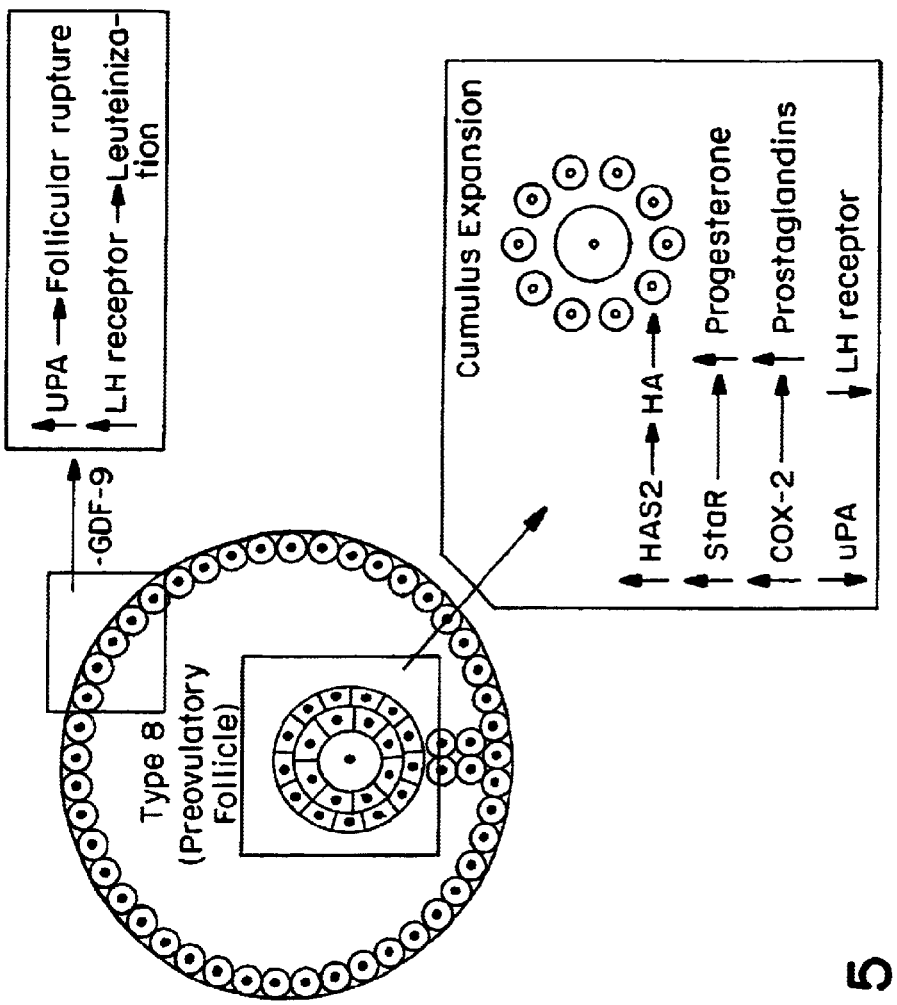
FIG. 5 is a model showing the roles of GDF-9 in the mammalian ovary.

As described herein, in situ hybridization analysis of LH receptor in pre-ovulatory follicles demonstrates that LH receptor is suppressed in the cumulus cells but not the mural granulosa cells, whereas after LH treatment in vivo, COX2 expression is highest in the cumulus cells. As also described herein, recombinant GDF-9 suppresses LH receptor mRNA but induces COX-2 expression, mimicking the normal expression of these genes in the cumulus cells. However, Eppig and colleagues (Eppig, J. J. et al., *Biol. Reprod.*, 56:976–984 (1997) and Eppig, J. J. et al., *Mol. Reprod Dev.*, 49:327–332 (1998)) elegantly demonstrated that full-grown oocytes suppress LH receptor mRNA expression, but that oocytes from preantral follicles, metaphase II arrested oocytes, or 2-cell embryos were not as effective. As described in knockout studies (Dong, J., et al., *Nature*, 383:531–535 (1996) and Elvin, J. A. et al., *Mol. Endocr.* (Submitted) (1999)) and herein, GDF-9 can stimulate changes in cell morphology, gene expression, and steroid production indicating that granulosa cells, at least from primary follicles and from antral follicles, possess receptors which bind GDF-9 (see FIG. 5 for a summary of the findings described herein). Since GDF-9 dramatically increases the level of COX-2 expression, it is unclear why COX-2 expression is not expressed at earlier stages of folliculogenesis or why earlier stage oocytes (Eppig, J. J. et al., 1997 *Biol. Reprod.*, 56:976–984 (1997); Eppig, J. J. et al., *Human Reprod.*, 12: 127–132 (1997) and Eppig, J. J., et al., *Mol. Reprod. Dev.*, 49:327–332 (1998)) are less effective in suppressing LH receptor. Although GDF-9 protein is detected at the immunohistochemical level at all stages of folliculogenesis, this does not necessarily prove that GDF-9 is active at all of these stages. One possibility is that the GDF-9 precursor is only processed to an active mature dimer at the type 3b stage and at the antral follicle stage. The regulation of the GDF-9 processing enzyme would be one way to regulate the activity of GDF-9 post-translationally. An alternative explanation is that both GDF-9-regulated and GDF-9-independent transcription factors function together to regulate the synthesis of COX-2. At least one regulator of COX-2 is the transcription factor enhancer-binding protein P (C/EBPβ). C/EBPβ, which is induced between 4 and 7 hours after hCG treatment, binds to the COX-2 promoter to downregulate COX-2 mRNA expression. COX-2 expression in the ovary normally peaks at 4 hours after hCG treatment while COX-2 protein continues to be present in the cumulus cells after ovulation (Lim, H., et al., Cell, 91:197–208 (1997)). However, in the C/EBPβ knockout mouse [which are infertile [Sterneck, 1997 #279]], levels of COX-2 mRNA remain elevated. COX-2 knockout mice are also infertile due to defects in ovulation and impaired oocyte maturation (Lim, H., et al., Cell, 91:197–208 (1997)). These studies from the C/EBPβ and COX-2 knockout models suggest that appropriate regulation of COX-2 in the cumulus cells is necessary to maintain the optimal micro environment of prostaglandins around the oocyte. GDF-9 appears to be one of the factors involved in induction of COX-2, and C/EBPβ plays a role in down regulation of COX-2. The studies described herein and those of ohers (Lawrence, T., et al., Endocr., 106:1114–1118 (1980) and Meduri, G., et al., Endocr., 131:366–373 (1992)) also suggest that LH regulates the expression of both COX-2 and C/EBPβ in cumulus cells indirectly because LH receptors are not present on these cells. However, it is unclear how this is achieved or how COX-2 is turned on rapidly and C/EBPβ more slowly.

Example 4

Molecular Characterization of the Follicle Defects in the Growth Differentiation Factor 9-Deficient Ovary Materials and Methods Experimental Animals.

All experimental mice were maintained in accordance with the NIH Guide for the Care and Use of Laboratory Animals. Unless otherwise indicate, ovaries from adult C57B1/6/129SvEv hybrid mice 6–12 weeks of age were used for both RNA isolation and specimens for in situ hybridization and immunohistochemistry. For the studies of COX-2, 3 week old mice received intraperitoneal injections of 7.5 IU Gestyl (Diosynth, B. V., Holland), then with 5 IU of hCG (Sigma, St. Louis, Mo.) 48 hours later. Ovaries were collected 5 hours after hCG injection.

RNA Isolation and Northern Blot Analysis.

Total RNA was extracted from various tissues of wild-type and GDF-9-deficient C57B1/6/129SvEv hybrid mice using RNA STAT-60 (Leedo Medical Laboratories, Houston, Tex.) as described by the manufacturer and quantitated on a spectrophotometer. 15 µg of total RNA of each sample were electrophoresed on a 1.2% agarose/7.6% formaldehyde gel and transferred to Hybond N nylon membrane (Amersham, Arlington Heights, Ill.). Table 2 includes a summary of all the specific cDNA fragments used to make probes in these studies. Probes were generated by random priming with {α-$^{32}$P}dATP using the Strip-EZ probe synthesis kit (Ambion, Austin, Tex.). The membrane was hybridized, washed, and subjected to autoradiography as described (Mahmoudi, M. and Lin, V. K., Biotech., 7: 331–332 (1989)). The probe was removed from the membrane using the Strip-EZ removal reagents (Ambion) following the manufacturer's protocol. The same blots were then reprobed with glyceraldehyde-3-phosphate dehydrogenase (GAPDH) or 18S ribosomal RNA as a loading control. Signals for each probe were quantitated on a Molecular Dynamics photodensitometer.

TABLE 2

Northern and In situ Probes. All probes used in this manuscript are murine

| PROBE | LENGTH (bp) | SOURCE | REFERENCE |
|---|---|---|---|
| p27 | 594 | Dr. W. Harper | 1–594 of U09968 |
| P-450 17α-OH | 522 | Subcloned from cDNA from Dr. A. Payne | 0–522 of M64863 |
| c-kit | 462 | PCR | 1050–1512 of Y00864 |
| Kit ligand | 476 | PCR | 78–554 of M57647 |
| Inhibin α | 630 | Subcloned from gene | 931–1043 of M95526 |
| Activin βA | 425 | Subcloned from cDNA | 1049–1474 of X69619 |
| Activin βB | 836 | PCR | 1–602 of X83376 +240 bp upstream |
| Follistatin | 1032 | PCR | 1–1032 of Z29532 |
| ERβ | 437 | Dr. S. K. Dey | 164–511 of AJ000220 |
| FSHR | 800 | PCR | ~740–1500 of Rat FSHR |
| P-450 Aromatase | 618 | PCR | 42–660 of D00659 |
| COX-2 | 864 | Dr. S. K. Dey | 56–929 of M94967 |
| LHR | 750 | PCR | 592–1331 of M81310 |
| IGF-I | 376 | Drs. J. Zhou & C. Bondy | Zhou, J., et al., Endocrinol., 129:3281–3288 (1991) |

In situ Hybridization.

In situ hybridization was performed essentially as described previously (Albrecht, U., et al., "Visualization of gene expression patterns by in situ hybridization", In: G. P. Daston (ed) Mol. Cell. Meth. Dev. Toxic., CRC Press, Boca Raton, Fla., pp. 23–48. (1997)) with the following modifications. Freshly dissected ovaries from wild-type or GDF-9-deficient C57B1/6/129SvEv hybrid mice were fixed in 4% paraformaldehyde-PBS overnight, processed, and embedded in paraffin. 5 µm thick sections were cut and pretreated as described. Table 2 includes a summary of the specific probe information. {α$^{35}$S} UTP-labeled antisense and sense probes were generated using the Riboprobe T7/T3 or Riboprobe T7/SP6 Combination System (Promega, Madison, WI). Hybridization was carried out at 55° C. with 5×10$^6$ cpm of each riboprobe per slide for 16–18 hrs in 50% deionized formamide/0.3M NaCl/20 mM TrisHCl (pH 8.0)/5 mM EDTA/10 mM NaPO4 (pH 8.0)/10% Dextran sulfate/1× Denhardt's/0.5 mg/ml yeast RNA. High stringency washes of 2×SSC/50% formamide and 0.1×SSSC at 65° C. were carried out. Dehydrated sections were dipped in NTB-2 emulsion (Eastman Kodak, Rochester, N.Y.) and exposed 2–14 days, depending on the probe, at 4° C. After developing, the slides were counterstained with hematoxylin and mounted for photography.

Immunohistochemistry.

Ovaries were fixed in 20% neutral buffered formalin for 3 hours, processed, and embedded in paraffin, and sectioned at 4 µm thickness. Detection of PCNA was conducted as previously described (Robker, R. L., and Richards, J. S., Mol. Endocr., 12:924–940 (1998)) using a mouse anti-PCNA monoclonal antibody (Novocastra Laboratories, Newcastle upon Tyne, UK). The rabbit anti-mouse P-450scc polyclonal antiserum was a kind gift from Michael J. Soares at the University of Kansas Medical Center, and used at a 1:625 dilution in 1×PBS, 0.05% Tween-20 (PBST), with 2% normal mouse serum (Sigma) and 2% normal goat serum (Vector Laboratories, Burlingame, Ga.). Rabbit anti-Ki-67 polyclonal antiserum (Novocastra) was diluted 1:300 and rabbit anti-p27 polyclonal antiserum (Santa Cruz Biotechnology, Inc., Santa Cruz, Calif.) was diluted 1:125 in 1% BSA, 0.1% NaN3 in PBS, with 2% normal mouse serum and 2% normal goat serum. Successful staining for both Ki67 and p27 required antigen retrieval methods. For Ki-67 staining, sections were steamed for 35 minutes in 0.1 M citrate buffer pH 6.0. For p27 staining sections were steamed for 35 minutes in pH 8.0 Tris-EDTA antigen retrieval solution. For Ki-67, p27 and P-450scc, all sections were blocked for 30 minutes in 1×PBS with 0.05% Tween-20, 2% normal mouse serum (Sigma) and 2% normal goat serum, and incubated in the primary antibody for 1 hour at room temperature. PCNA detection was accomplished using the Super Sensitive Mouse Antibody Animal Detection kit (Biogenex, San Ramon, Calif.) containing anti-mouse IgG biotinylated secondary antibody preabsorbed with rat tissue. P-450scc, p27, and Ki-67 antibodies were detected using the Super Sensitive Rabbit Antibody Detection kit (Biogenex) containing anti-rabbit IgG biotinylated secondary antibody preabsorbed with mouse tissue. PCNA and P-450scc were detected using streptavidin-conjugated alkaline phosphatase label and New Fuschin substrate (Biogenex) while p27 was detected with streptavidin-conjugated horseradish peroxidase label (Biogenex) and DAB substrate (Vector Laboratories).

TUNEL Assay.

Ovaries were stained for apoptotic cells by a modified TUNEL method using the Apoptag Plus Complete Apoptosis Detection kit (Oncor Laboratories, Gaithersburg, Md.) following the manufacturer's instructions. Nuclei were counterstained with Propidium iodide/Antifade mounting media (Oncor Laboratories).

RT-PCR Analysis.

Oligo-dT primed cDNA from 1 $\mu$g of either control or GDF-9-deficient ovarian RNA was synthesized using Superscript reverse transcriptase (GibcoBRL) following the manufacturer's protocol. 1 $\mu$l of each RT reaction (1/20of total) was used in each 25 $\mu$l PCR reaction primed with kit ligand-specific oligonucleotides: 5'CCAGAAACTAGATC-CTTTACTCCT 3' (SEQ ID NO: 17) (sense—nts 493–517 of S40364) and 5' CTGTTGCAGCCAGCTCCCTTAG 3' (SEQ ID NO: 18) (antisense 943–919 of S40364) primers which span introns and an 84 bp alternatively spliced exon. Amplification of the KL-1 form yields a product of 450 bp, and amplification of KL-2 form yields a product of 366 bp. Products were separated on a 2% agarose gel and visualized by ethidium bromide staining.

Results

Cell Cycle Progression

GDF-9-deficient follicles with intact oocytes contain only one layer of granulosa cells, and fail to form follicles consisting of multiple layers of granulosa cells. Proliferating cell nuclear antigen (PCNA), a cofactor of DNA polymerase $\delta$ and cyclin-cdk complexes, is expressed during G1, increases through the G1/S transition, is high in G2, and declines sharply in M phases of the cell cycle (Oktay, K. et al., *Biol. Reprod.*, 53:295–301 (1995)). Similarly, Ki-67, a component of the granular nucleolus, is expressed in all cell cycle phases except G0 (Gerdes, J., et al., *J. Immunol.*, 133:1710–1715 (1984)). The most highly proliferative granulosa cells are found in the wild-type antral follicle, in which the majority of the granulosa cells are PCNA and Ki-67 positive. In type 3b (large one layer) and type 4 (2 layer) follicles of wild-type ovaries, immunohistochemical analysis of PCNA or Ki67 showed that >50% of the granulosa cells in the cross-sections are positive (i.e., positive defined as intense red staining of the nucleus; negative defined as light or diffuse staining of the nucleus and cytoplasm). In contrast, the type 3b follicles with intact oocytes in the GDF-9-deficient ovary demonstrated <10% positive staining granulosa cells/cross-section indicating that nearly all of the granulosa cells are blocked at G0. However, soon after oocyte degeneration, granulosa cell differentiation began to occur in the follicles of the GDF-9-deficient ovary, and more cell nuclei stained positively for both PCNA and Ki-67. Oocyte nuclear staining with the PCNA antibody was detected in growing and full grown oocytes of GDF-9-deficient type 3a and 3b follicles, consistent with previous studies demonstrating the presence of PCNA in nuclei of oocytes of primary through antral follicles in wildtype ovaries (Oktay,K. et al., Biol. Reprod., 53:295–301 (1995)).

TUNEL Labeling

Although normal follicular development in the GDF-9-deficient ovaries arrests at the type 3b stage and oocyte loss eventually results in granulosa cell "differentiation", histological examination of the GDF-9-deficient ovaries surprisingly failed to detect any apoptotic-appearing cells. To confirm the relative absence of apoptotic cells in the GDF-9-deficient ovaries, a TUNEL assay was used to fluorescently label DNA ends. Granulosa cells of wild-type atretic antral follicles and corpora lutea contained many positively labeled cells. In contrast, sections of GDF-9-deficient ovaries contained 2–10 positively labeled cells per ovarian section. No positively staining cells were found in the one-layer follicles, but an occasional apoptotic cell was seen in follicles with degenerating oocytes, within the steroidogenic follicular nests, or within the interstitial tissue. Thus, in the absence of GDF-9, once the type 3b follicle stage is reached, the majority of granulosa cells remain dormant and fail to either proliferate or die.

Analysis of Cell Cycle Inhibitors p21 and p27 are well documented inhibitors of the cell cycle, and are correlated with cell cycle arrest upon luteinization in the ovary (Robker, R. L. and Richards, J. S., Biol. Reprod., 59:476–482 (1998)). Based on the relative lack of proliferation of the granulosa cells in the GDF-9 knockout ovaries, expression of both p21 and p27 mRNA was examined by in situ hybridization and p27 protein by immunohistochemistry. p21 mRNA was detected at low levels ubiquitously in both wild-type and GDF-9-deficient ovaries with higher levels in wild type atretic follicles and scattered cells in the corpora lutea, and in the luteinized follicular nests of the GDF-9 deficient ovary. In wild-type ovaries, p27 mRNA was also expressed ubiquitously at low levels throughout the ovary but was more abundant in the corpora lutea of wild-type ovaries. In the GDF-9-deficient ovary, granulosa cells of the one-layer follicles expressed detectable levels of p27 message, while small groups of cells in the center of the GDF-9-deficient ovary expressed higher levels. Similarly, nuclear p27 immunoreactivity was clearly detectable in the majority of luteinized granulosa cells within the wildtype corpus luteum, and within the luteinized follicular nests of the GDF-9-deficient ovary. Reduced p27 nuclear staining was also present in granulosa cells of both wildtype and GDF-9-deficient one-layer follicles, which was clearly higher than the staining in the negative control or in the interstitial cells. Although it is impossible to estimate protein levels by immunohistochemistry, there does not appear to be a dramatic difference in p27 immunoreactivity between the one-layer follicles of the GDF-9 knockout and wild-type ovaries. This indicates that p27 protein overexpression is not the reason for the block in folliculogenesis at the primary follicle stage in the GDF-9-deficient ovaries.

Thecal Layer Development

It has been previously reported that a morphologically distinct thecal layer could not be detected by light and electron microscopic analysis in GDF-9-deficient ovaries (Dong, J., et al., *Nature* 383: 531–535 (1996)). However, a flattened layer of fibroblastic cells outside of the granulosa cell basement membrane rings the type 3b follicles in the GDF-9-deficient ovaries. In situ hybridization was carried out with a probe for 17 α-hydroxylase cytochrome P-450 (17α-OH), a theca cell-specific enzyme necessary for androgen production, to confirm the absence of a true thecal layer. In the wild-type ovary, cells expressing 17α-OH began to associate with type 3b and type 4 follicles, and form complete rings just outside the granulosa cell basement membranes by the multilayer preantral follicle stage. In contrast, in the GDF-9-deficient ovaries, only a few cells expressing 17α-OH were present and scattered in the interstitium, which are not associated with follicles. It is likely that these 17α-OH-positive cells represent a theca cell precursor population that is responding to the elevated serum LH ((Dong, J., et al., *Nature* 383: 531–535 (1996)). Similarly, absence of LH receptor and c-kit mRNA around the follicle (see below) confirms that a theca cell layer fails to form. These data indicate that GDF-9 signaling is required either directly or indirectly to recruit theca cell precursors to the early preantral follicles.

Analysis of c-Kit and Kit Ligand Expression

The c-kit/kit ligand-signaling pathway has been shown to be important for germ cell proliferation and folliculogenesis (Besmer, P., et al., *Dev. Suppl.*, 125–137 (1993); Huang, E. J. et al., *Dev. Biol.*, 157:100–109 (1993) and Kuroda, H., et al., *Dev. Biol.*, 126:71–79 (1988)). By northern blot analysis, it was shown that c-kit mRNA is expressed in GDF-9-deficient ovaries and that levels are comparable to or slightly higher than wildtype ovaries. By in situ hybridization, c-kit mRNA was localized to the oocyte and theca-interstitial cells of the wild-type ovary, but was excluded from granulosa cells as previously demonstrated (Manova, K., et al., *Devel.*, 110:1057–1069 (1990)). In the GDF-9-deficient ovaries, c-kit mRNA localized only to oocytes, with only background levels of silver grains present over other cell types.

In contrast to the c-kit expression results, kit ligand expression in GDF-9-deficient ovaries was increased 32-fold compared to expression in wild-type ovaries. IGF-1, which is also expressed in the granulosa cells of early preantral follicles, however, did not show a similar increase in expression in the GDF-9-deficient ovary, suggesting that the increase in kit ligand represented a specific regulatory interaction, rather than a tissue composition effect. Although in situ hybridization is not a reliable method for quantitating MRNA expression, relative expression levels between wild-type and GDF-9-deficient ovaries can be compared by positioning sections from both types of ovaries close together on the same slide to minimize inter-slide variability in hybridization efficiency and emulsion thickness. Under these conditions, kit ligand expression was barely detected in the wild-type ovary, with a faint signal above background apparent in granulosa cells of preantral follicles. In contrast, in the GDF-9-deficient ovaries, granulosa cell expression of kit ligand was abundant. Type 3a and early type 3b follicles had detectable levels of kit ligand, while the largest one-layered follicles showed more intense staining. In the event that paracrine factors produced by multi-layered follicles of adult ovaries repressed kit ligand expression, ovaries from 10, 17, and 28 day old wild-type mice were examined. Although kit ligand was somewhat easier to detect in these immature ovaries due to the increased number of preantral follicles, the relative expression level per follicle was never comparable to the level seen in the GDF-9-deficient ovaries at similar ages. Kit ligand expression was increased further in the granulosa cells in asymmetric follicles, which are presumably destined to undergo oocyte degeneration. However, soon after the oocyte degenerated, kit ligand expression disappeared, and was also absent in the follicular nests.

There are two alternatively-spliced forms of KL, KL-1 and KL-2, which differ by 84 bp. This alternative splicing results in an additional 28 amino acids in KL-1, which includes a proteolytic cleavage site. Since membrane-bound KL is more active than free KL, KL-2, the more stable, cell-associated form is consequently more potent (Besmer, P., et al., *Dev. Suppl.*, 125–137 (1993)). By non-quantitative RT-PCR using primers that can distinguish KL-1 from KL-2, both forms of KL were detected in both the wild-type and GDF-9-deficient ovaries. Immunohistochemical analysis of the KL protein in the GDF-9-deficient ovaries demonstrated the same pattern of expression as the KL mRNA, with the most intense staining occurring in asymmetric follicles. Taken together, these results indicate that GDF-9 negatively regulates kit ligand expression in granulosa cells in a paracrine manner and that active KL protein is synthesized.

TGF-β Superfamilly Members (Activins, Inhibins, Follistatin)

Activins and inhibins have been implicated in the regulation of granulosa cell proliferation and follicle growth both in vivo and in vitro (Mather, J. P., et al., *Proc. Soc. Exp. Biol. Med.*, 215:209–222 (1997) and Matzuk, M. M., et al., *Rec. Prog. Horm. Res.*, 51:123–157 (1996)). The expression levels and pattern of expression of inhibin α, activin βA, activin βB, and the activin binding protein, follistatin, were examined in wild-type and GDF-9-deficient ovaries. By northern blot analysis, surprisingly inhibin α was expressed at similar levels in GDF-9-deficient versus wild-type ovaries. In wild-type ovaries, inhibin α was expressed in granulosa cells of all growing follicles (type 3a through the pre-ovulatory stage), but was excluded from corpora lutea. In GDF-9-deficient ovaries, inhibin α was expressed highly in the one-layer follicles, in the follicles with degenerating oocytes, and in the central steroidogenic follicular nests. This indicates that the cells of the follicular nests, although similar to corpora lutea in many respects, are developmentally different than granulosa cells in wild-type ovaries which have proliferated, formed into multilayer follicles, and associated with an active thecal layer before luteinizing.

The two inhibin/activin β subunits, βA and βB, and the activin binding protein, follistatin, were expressed in overlapping patterns in the wild-type ovary. All three genes were expressed in granulosa cells of multilayer preantral and antral follicles. Interestingly, expression of βB in atretic follicles was low and localized specifically to the peri-oocyte cells, while in healthy follicles, all granulosa cells expressed high levels. GDF-9-deficient ovaries had almost undetectable βB message by northern blot analysis and very low levels of follistatin, which localize weakly to the granulosa cells of the one-layer follicles and more robustly to follicles with degenerating oocytes and at highest levels in oocyte-deficient follicular nests. βA message was not detectable in the one-layered follicles, weakly localized to granulosa cells of follicles with degenerating oocytes, and was expressed at high levels in oocyte-deficient follicular nests. However, by northern blot analysis the levels of βA expression were equivalent between GDF-9-deficient and wild-type ovaries. These results indicate that the GDF-9-deficient ovaries have retained the ability to make both activin β and inhibin α subunits.

Characterization of Antral Follicle Markers (ERβ, FSHR, Aromatase Cytochrome P450)

To further characterize the follicles of the GDF-9-deficient ovary, the expression of other markers associated with antral granulosa cell functional differentiation was analyzed: FSH receptor (FSHR), aromatase cytochrome P-450 (aromatase), and estrogen receptor β (ERβ). It has been previously shown by northern blot analysis that FSHR is expressed similarly in both GDF-9-deficient and wild-type ovaries, and that aromatase expression is 50% of the wild-type level (Dong, J., et al., Nature, 383:531–535 (1996)). ERβ was also expressed at low but similar levels in the knockout versus wild-type ovaries. By in situ hybridization in the wild-type ovary, FSHR, ERβ, and cytochrome aromatase were detected specifically in the granulosa cells as previously reported (Richards, J. S., Endocrine Reviews, 15:725–751 (1994); Byers, M., et al., Mol. Endocr., 11: 172–182 (1997) and Camp T., et al., Mol. Endocr., 5:1405–1417 (1991)). ERβ was expressed at low levels in one-layer follicles, and at higher levels in multilayer follicles. FSHR was expressed in multilayer preantral and antral follicles. Aromatase, which is normally induced by FSH stimulation of the granulosa cells, was expressed at high levels specifically in the pre-ovulatory follicle. In the GDF-9-deficient ovary, ERβ was expressed at low levels in the one-layer follicles, and at somewhat higher levels in the follicles with degenerating oocytes. FSHR was also expressed in the follicles with degenerating oocytes, while aromatase was expressed at high levels only in the follicular nests with completely degenerated oocytes. Aromatase expression in these follicular nests in the GDF-9-deficient ovaries indicates that a functional FSH signaling pathway is present similar to granulosa cells of pre-ovulatory follicles of a wild-type ovary.

Characterization of Per-ovulatory and Luteal Markers (COX-2, LHR, Cholesterol Side Chain Cleavage Cytochrome P-450)

As mentioned previously, GDF-9-deficient ovaries contain multiple, centrally located nests of cells that have the appearance of luteinized granulosa cells. By electron microscopic analysis, the cells of these nests contain multiple lipid droplets and mitochondria with tubular cristae typical of highly steroidogenic cells (Dong, J., et al., Nature, 383:531–535 (1996)). To confirm their steroidogenic nature and similarity to luteal cells, the expression of cyclooxygenase 2 (COX-2) and LH receptor (LHR) message, and cholesterol side chain cleavage cytochrome P-450 protein (P-450scc) was analyzed. As COX-2 is expressed in the wild type ovary only within a discrete window of time following the LH surge (Sirois, J., et al., J. Biol. Chem., 267:11586–11592 (1992) and Sterrieck, E., et al., Genes Dev., 11:2153–2162 (1997)), ovaries from 3 week old mice stimulated for 48 hours with PMSG, then hCG for 5 hours were used for both northern blot analysis and in situ hybridization. By northern blot analysis, RNA from superovulated ovaries showed three distinct bands, while no bands could be detected in the unstimulated wild type or GDF-9-deficient ovary lanes. Consistent with the northern blot data, in situ hybridization showed that in wild-type ovaries stimulated with PMSG and hCG, COX-2 is expressed by the granulosa cells of pre-ovulatory follicles (Sterrieck, E., et al., Genes Dev., 11:2153–2162 (1997)). The highest expression at 5 hours occurred in the cumulus cells of the wild type ovary, while COX-2 expression was completely undetectable in the GDF-9-deficient ovary.

In contrast to the above-mentioned COX-2 expression data, it has been previously shown that LHR is expressed in the GDF-9-deficient ovary at levels comparable to the wild-type ovary by northern blot analysis (Dong, J., et al., Nature, 383:531–535 (1996)). LHR was expressed by theca cells, granulosa cells of pre-ovulatory follicles and luteinized granulosa cells of corpora lutea (Sirois, J., et al., J. Biol. Chem., 267:11586–11592 (1992)). In the GDF-9-deficient ovary, granulosa cells of nonluteinized and luteinized follicular nests expressed LHR at very high levels. Stimulation of theca and luteinized granulosa cells by LH stimulates production of the steroidogenic enzyme P-450scc and subsequent synthesis of progesterone (Richards, J. S., Endocrine Reviews, 15:725–751 (1994)). In wild-type ovaries, P-450scc protein was present in theca cells, corpora lutea, and secondary interstitial tissue. In GDF-9-deficient ovaries, P-450scc protein was detected at low levels in nonluteinized follicular nests and at much higher levels in the steroidogenic "luteinized" follicular nests. Female 6 week old GDF-9-deficient mice had average serum progesterone levels of 3.4 ng/ml, compared to 2.6 ng/ml in wild-type mice, indicating that these nests are not only capable of expressing markers but also functioning like "miniature" corpora lutea. However, as mentioned earlier, these follicular nests also express inhibin α, a marker that is normally never observed at significant levels in corpora lutea.

Discussion

Figure 6:
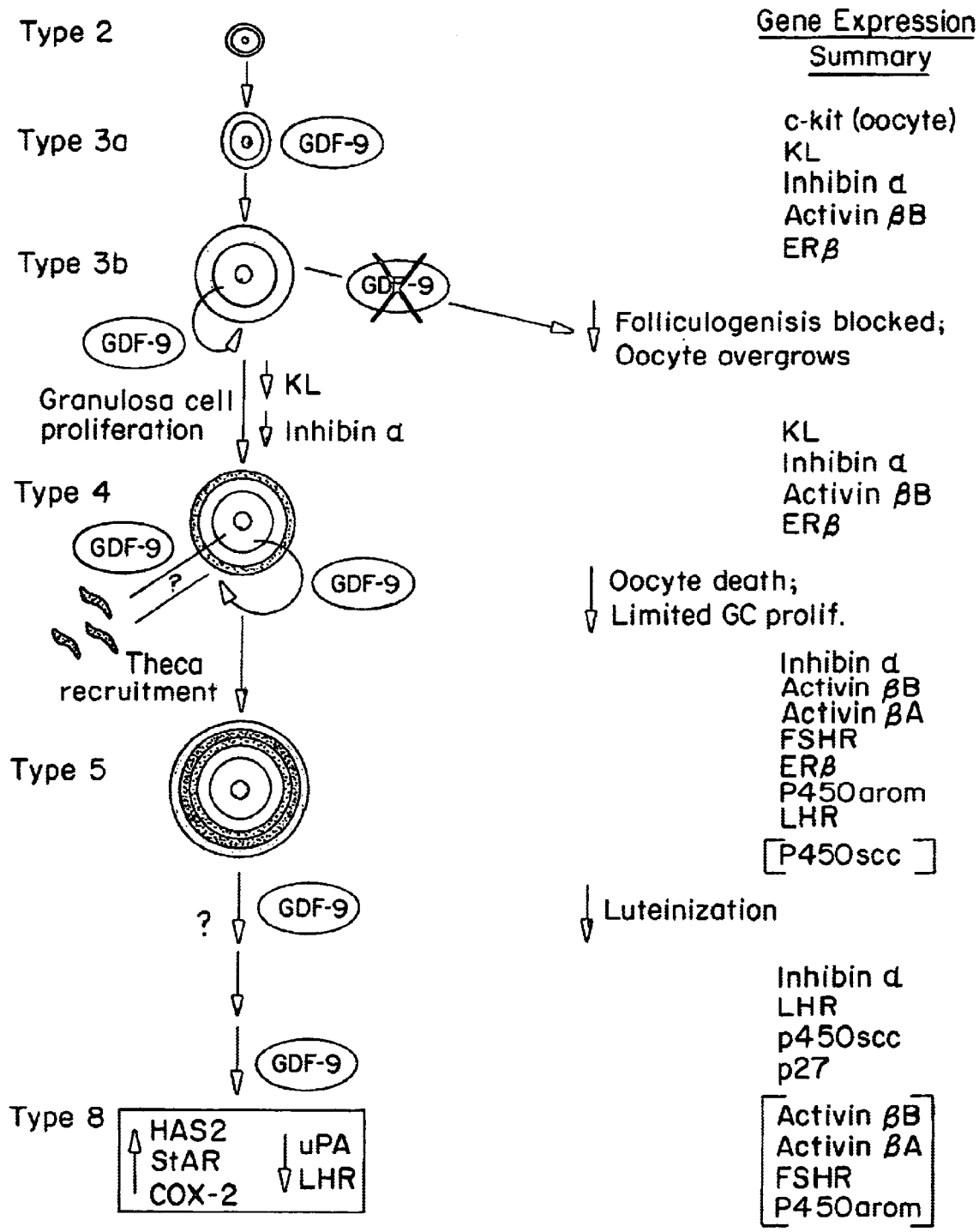
FIG. 6 is a summary of the GDF-9 knockout ovary studies.

It has been previously demonstrated that absence of GDF-9 in the mammalian oocyte leads to infertility due to a block in follicular development. As summarized in FIG. 6, the defects at the molecular level have been further characterized. GDF-9 mRNA (McGrath, S. A., et al., Mol. Endocr., 9:131–136 (1995)) and protein (Elvin, J. A., et al., Mol. Endocr., (Submitted) (1999)) are absent in primordial follicles and are first observed in type 3a primary follicles. Ovaries from the GDF-9 knockout mice show a block at the type 3b primary follicle stage. As demonstrated herein, the granulosa cells of the type 3b follicle essentially lay dormant; neither cell division nor apoptosis is observed in the granulosa cells of the follicles until the oocyte is lost. Thus, although, GDF-9 protein is synthesized at the type 3a stage, the GDF-9 signal transduction cascade must only become essential at the type 3b stage for further follicular growth. Clearly, these studies suggest that recruitment of primordial follicles and growth of the granulosa cells from the primordial follicle stage (<20 granulosa cells) to the type 3b stage (90 granulosa cells) (Pedersen, T., "Follicle Growth in the Mouse Ovary", In: S. A. Bigger JD (ed) Oogenesis, University Park Press, Baltimore, pp. 361–376. (1972)) are not dependent on GDF-9.

Unlike the dramatic apoptosis observed in atretic follicles of wild-type ovaries, there is minimal apoptosis observed in the GDF-9 knockout ovary. Normally, apoptosis occurs in antral follicles at a point after they become responsive and dependent on FSH. Even though granulosa cells of the GDF-9-deficient ovary express antral markers, apoptotic cells were rarely seen. These observations lead to several alternative explanations. GDF-9 may be required to induce competence to respond to pro-apoptotic stimuli. Alternatively, although the elevated serum FSH (Dong, J., et al., Nature, 383:531–535 (1996)) cannot overcome the type 3b block, it could promote granulosa cell survival. Finally, the granulosa cells in the GDF-9-deficient ovaries may bypass this "apoptosis-competent" state by differentiating after the oocyte degenerates to form the steroidogenic follicular nests. Thus, GDF-9 is an important factor for the "differentiation" of the granulosa cells, allowing the posttype 3b granulosa cells to acquire specific characteristics such as the capability to undergo apoptosis.

It has previously been hypothesized that an oocyte-derived factor regulates kit ligand expression by a paracrine mechanism (Packer, A. I., et al., Dev. Biol., 161:194–205 (1994)). In gonadotropin-stimulated mice, there is a gradient of kit ligand expression whereby granulosa cells farthest from the oocyte (i.e., mural granulosa cells) express the highest levels while those closest to the oocyte (i.e., cumulus cells) express very low or undetectable levels (Motro, B. and Bernstein, A., Dev. Dyn., 197:69–79 (1993)). The dramatically elevated kit ligand in GDF-9-deficient follicles demonstrated herein indicates that GDF-9 is one of the oocyte-secreted paracrine factors that negatively regulates kit ligand expression. This hypothesis is supported by evidence from our in vitro studies of GDF-9 action described herein demonstrating that GDF-9 can regulate other genes (i.e., hyaluronan synthase 2, cyclooxygenase 2, steroidogenic acute regulator protein, urokinase plasminogen activator, and luteinizing hormone receptor) which are differentially expressed with respect to the oocyte in antral follicles. Thus, it is likely that action of other oocyte-produced and extrafollicular factors unopposed by GDF-9 contribute to the increased kit ligand expression observed herein. The kit ligand that is produced in the GDF-9-deficient ovaries also appears to be active. GDF-9-deficient ovaries contain significantly more mast cells per section, likely due to kit ligand stimulated increased recruitment and proliferation as has previously been reported in other systems. In addition, kit ligand has also been shown to stimulate oocyte growth in vitro (Packer, A. I., et al., Dev. Biol., 161:194–205 (1994)). The oocytes in the GDF-9-knockout ovary grow more rapidly and to a 15% greater maximum size compared to the controls (Carabatsos, M., et al., Dev. Biol., 203:373–384 (1998)), before ultimately degenerating, providing further evidence of functional granulosa cell derived kit ligand signaling through c-kit on the oocyte. As demonstrated herein by Northern blot analysis, other members of the TGF-$\beta$ superfamily continue to be expressed in the GDF-9-deficient ovary. By northern blot analysis, inhibin $\alpha$ and activin $\beta$A subunits are expressed in GDF-9-deficient ovaries at similar levels to controls, whereas activin $\beta$B and follistatin are dramatically decreased. In vitro activin A has been shown to stimulate follicular growth (Mather et al., 1997) and to enable FSH stimulation of granulosa cell DNA synthesis (Miro, F. and Hillier, S., Endocr., 137: 464–468 (1996)). Additionally, activin A+FSH stimulate granulosa cells from immature follicles to produce progesterone, but decreased progesterone synthesis by granulosa cells from differentiated culture with or without FSH (Miro, F., et al., Endocr., 129:3388–3394 (1991)). In the GDF-9-deficient ovary, it is likely that locally produced activin A in the follicular nests stimulate limited granulosa cell proliferation and enhances the response of these cells to the elevated serum gonadotropins to express P450 aromatase and P-450scc. It is also likely that he activin effect in the GDF-9-deficient ovaries is enhanced by the reduced level of follistatin, an activin binding protein and antagonist.

Example 5

Identification of a Stimulatory Effect of Recombinant mGDF-9 on Progesterone Synthesis by In Vitro Cultured Mural Granulosa Cells The effect of mGDF-9 on progesterone production occurs only in the absence of or at low doses (0.5 or 1 ng/ml) of follicle stimulating hormone (FSH). At higher doses of FSH (5 ng/ml and 10 ng/ml) there is no significant difference in progesterone production between FSH alone or FSH+ mGDF-9. FSH, as has been shown previously (Oonk, et al.), appears to stimulate P450 cholesterol side chain cleavage expression, the enzyme which catalyzes the rate-limiting step in the cholesterol biosynthetic pathway. Based on very recent data, progesterone stimulation by GDF-9 appears to be due to stimulation of steroidogenic acute regulatory protein (STAR), an enzyme which has been shown to be involved in mobilizing or transporting cholesterol within the cell, but not P450scc.

Example 6

Identification of a Stimulatory Effect of Recombinant mGDF-9 on Follistatin and Activin $\beta$B Expression by In Vitro Cultured Mural Granulosa Cells Protocol Primary granulosa cells were isolated from 8 pairs of ovaries as described above and cultured for 5 hours with or without 50–60 ng/ml recombinant mGDF-9 in $\alpha$-MEM based media containing 4 ng/ml of FSH without fetal calf serum. After culture the media was removed and non-adherent cells were collected by centrifugation. RNA was isolated using Qiagen RNEasy total RNA isolation kit. This RNA was reverse transcribed into cDNA which was used to generate probes for hybridization to the Affymetrix developmental biology 250 gene chip. Based on the results of this initial screening method, the granulosa cell culture experiment was repeated and RNA was prepared and used for Northern blot analysis.

Results

According to the developmental chip analysis, recombinant mGDF-9 stimulated a 4.9 fold increase in follistatin {191 (mGDF-9 treated): 39 (control)} and a 3.3 fold increase in activin $\beta$B {65 (mGDF-9 treated): 20 (control)} expression by in vitro cultured primary granulosa cells (FIG. 3/15-1). This result was confirmed by northern blot analysis (FIG. 3/15-2). Densitometric analysis of these northern blots indicated that mGDF-9 treatment stimulated a 3.1 fold increase in follistatin expression and a 3.3 fold increase in activin ,B expression. Additionally, follistatin expression responded to mGDF-9 in a dose dependent fashion (FIG. 3/15-3). These results are further supported by northern blot analysis of total RNA isolated from our GDF-9-deficient mouse ovaries which show a ~3-fold decrease in follistatin and ~6-fold decrease in activin $\beta$B expression in vivo in the absence of GDF-9.

Significance

The current data showing regulation of follistatin and activin $\beta$B by mGDF-9 confirm our previous results that the recombinant GDF-9 protein that we are producing is biologically active. Radioimmunoassays are available to analyze protein production for both follistatin and activin $\beta$B, providing two additional assays for GDF-9 agonists and antagonists. Additionally, these results provide two additional downstream targets which can be used to identify GDF-9 response elements for transcriptional regulation and understand GDF-9 signal transduction.

Example 7

Identification of an Inhibitory Effect of Recombinant mGDF-9 on Luteinizing Hormone Receptor (LHR) Expression by In Vitro Cultured Mural Granulosa Cells Protocol Granulosa cells were isolated and cultured as described previously for varying lengths of time with fetal calf serum, +/−FSH. RNA was isolated as described and RT-PCR for LHR message was done as described using intron spanning primers.

Results

LHR expression increases with increasing culture time in control cultures (FIG. 3/15-4). However, LHR expression in cultures treated with 50 ng/ml mGDF-9 is suppressed.

Significance

It has been previously shown that LHR expression in vivo is rarely if ever detected on cumulus granulosa cells (those in immediate contact with the oocyte) and increases with increasing distance from the oocyte. In a recent study (Eppig, et al., 1997), it was shown that an oocyte-secreted factor had the ability to inhibit LHR expression. The results described herein indicate that GDF-9 is the oocyte-secreted factor which normally inhibits LHR expression.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

---

What is claimed is:

1. A method of identifying an agent which alters activity of GDF-9 comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the granulosa cells wherein expression of a gene within the granulosa cells is modulated due to the binding of GDF-9 to the cells; and
   c) determining the extent to which expression of the gene regulated by binding of GDF-9 to the receptors occurs upon binding of GDF-9 to the receptors on the granulosa cells,
wherein alteration of expression of the gene upon binding of GDF-9 to the receptors in the presence of the agent to be assessed indicates that the agent alters GDF-9 activity.

2. The method of claim 1 wherein the extent to which expression of the gene occurs is determined by measuring the gene product.

3. The method of claim 2 wherein the gene encodes a protein selected from the group consisting of: hyaluronan synthase, steroidogenic acute regulatory protein, luteinizing hormone receptor, cyclooxygenase 2, urokinase plasminogen activator, kit ligand, activin/inhibin βB and follistatin.

4. The method of claim 1 wherein the extent to which expression of the gene occurs is determined by measuring a product or function which results from the activity of the gene of b).

5. The method of claim 4 wherein the product or function is selected from the group consisting of: hyaluronic acid, phosphorylated steroidogenic acute regulatory protein, progesterone, plasmin, prostaglandins, activin βB:activin βB, inhibin α:activin βB, products produced as a result of the binding of luteinizing hormone receptor, the binding of ligand to the luteinizing hormone receptor and the breakdown of plasminogen.

6. The method of claim 1 further comprising a step (d) of comparing the extent of expression in (c) with the extent to which expression occurs in a control sample.

7. A method of identifying an agent which is an inhibitor of GDF-9 activity comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the granulosa cells wherein expression of a gene within the granulosa cells is modulated due to the binding of GDF-9 to the cells; and
   c) determining the extent to which expression of the gene regulated by binding of GDF-9 to the receptors occurs upon binding of GDF-9 to the receptors on the granulosa cells,
wherein inhibition of expression of the gene upon binding of GDF-9 to the receptors in the presence of the agent to be assessed indicates that the agent inhibits GDF-9 activity.

8. The method of claim 7 wherein the extent to which expression of the gene occurs is determined by measuring the gene product.

9. The method of claim 8 wherein the gene encodes a protein selected from the group consisting of: hyaluronan synthase, steroidogenic acute regulatory protein, luteinizing hormone receptor, cyclooxygenase 2, activin/inhibin βB and follistatin.

10. The method of claim 7 wherein the extent to which expression of the gene occurs is determined by measuring a product or function which results from the activity of the gene of b).

11. The method of claim 10 wherein the product or function is selected from the group consisting of: hyaluronic acid, phosphorylated steroidogenic acute regulatory protein, progesterone, prostaglandins, activin βB:activin βB, inhibin α:activin βB, products produced as a result of the binding of luteinizing hormone receptor and the binding of ligand to the luteinizing hormone receptor.

12. The method of claim 7 further comprising a step (d) of comparing the extent of expression in (c) with the extent to which expression occurs in a control sample.

13. A method of identifying an agent which is an inhibitor of GDF-9 activity comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the granulosa cells wherein expression of a uPA gene is modulated due to the binding of GDF-9 to the cells; and
   c) determining the extent to which expression of the uPA gene regulated by binding of GDF-9 to the receptors occurs upon binding of GDF-9 to the receptors on the granulosa cells,
wherein an increase in production of uPA in the presence of GDF-9 indicates that the agent is an inhibitor of GDF-9 activity.

14. A method of identifying an agent which is an enhancer of GDF-9 activity comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the granulosa cells wherein expression of a gene within the granulosa cells is modulated due to the binding of GDF-9 to the cells; and
   c) determining the extent to which expression of the gene regulated by binding of GDF-9 to the receptors occurs upon binding of GDF-9 to the receptors on the granulosa cells, wherein enhanced expression of the gene upon binding of GDF-9 to the receptors in the presence of the agent to be assessed indicates that the agent is an enhancer of GDF-9 activity.

15. The method of claim 14 wherein the extent to which expression of the gene occurs is determined by measuring the gene product.

16. The method of claim 15 wherein the gene encodes a protein selected from the group consisting of: hyaluronan synthase, steroidogenic acute regulatory protein, luteinizing hormone receptor, cyclooxygenase 2, activin/inhibin βB and follistatin.

17. The method of claim 14 wherein the extent to which expression of the gene occurs is determined by measuring a product or function which results from the activity of the gene of b).

18. The method of claim 17 wherein the product or function is selected from the group consisting of: hyaluronic acid, phosphorylated steroidogenic acute regulatory protein, progesterone, prostaglandins, activin βB:activin βB, products produced as a result of the binding of luteinizing hormone receptor and the binding of ligand to the luteinizing hormone receptor.

19. The method of claim 14 further comprising a step (d) of comparing the extent of expression in (c) with the extent to which expression occurs in a control sample.

20. A method of identifying an agent which is an enhancer of GDF-9 activity comprising the steps of:
 a) combining:
  i) granulosa cells;
  ii) GDF-9; and
  iii) an agent to be assessed;
 b) maintaining the combination produced in (a) under conditions appropriate for binding of GDF-9 to receptors on the granulosa cells wherein expression of a uPA gene is modulated due to the binding of GDF-9 to the cells; and
 c) determining the extent to which expression of the uPA gene regulated by binding of GDF-9 to the receptors occurs upon binding of GDF-9 to the receptors on the granulosa cells,
wherein a decrease in production of uPA in the presence of GDF-9 indicates that the agent is an enhancer of GDF-9 activity.

21. A method of identifying an agent which inhibits fertility comprising the steps of:
 a) combining:
  i) granulosa cells;
  ii) GDF-9; and
  iii) an agent to be assessed;
 b) maintaining the combination produced in (a) under conditions appropriate for binding of GDF-9 to receptors on the granulosa cells wherein expression of a gene is modulated due to the binding of GDF-9 to the cells; and
 c) determining the extent to which expression of the gene regulated by binding of GDF-9 to the receptors occurs upon binding of GDF-9 to the receptors on the granulosa cells,
wherein inhibition of expression of the gene upon binding of GDF-9 to the receptors in the presence of the agent to be assessed indicates that the agent inhibits fertility.

22. The method of claim 21 wherein the extent to which expression of the gene occurs is determined by measuring the gene product.

23. The method of claim 22 wherein the gene encodes a protein selected from the group consisting of: hyaluronan synthase, steroidogenic acute regulatory protein, luteinizing hormone receptor, cyclooxygenase 2, activin/inhibin βB and follistatin.

24. The method of claim 21 wherein the extent to which expression of the gene occurs is determined by measuring a product or function which results from the activity of the gene of b).

25. The method of claim 24 wherein the product or function is selected from the group consisting of: hyaluronic acid, phosphorylated steroidogenic acute regulatory protein, progesterone, prostaglandins, activin βB:activin βB, inhibin α:activin βB, products produced as a result of the binding of luteinizing hormone receptor and the binding of ligand to the luteinizing hormone receptor.

26. The method of claim 21 further comprising a step (d) of comparing the extent of expression in (c) with the extent to which expression occurs in a control sample.

27. A method of identifying an agent which inhibits female fertility comprising the steps of:
 a) combining:
  i) granulosa cells;
  ii) GDF-9; and
  iii) an agent to be assessed;
 b) maintaining the combination produced in (a) under conditions appropriate for binding of GDF-9 to receptors on the granulosa cells wherein expression of a uPA gene is modulated due to the binding of GDF-9 to the cells; and
 c) determining the extent to which expression of the gene a uPA gene regulated by binding of GDF-9 to the receptors occurs upon binding of GDF-9 to the receptors on the granulosa cells,
wherein an increase in production of uPA in the presence of high concentrations of GDF-9 indicates that the agent inhibits fertility.

28. A method of identifying an agent which enhances fertility comprising the steps of:
 a) combining:
  i) granulosa cells;
  ii) GDF-9
  iii) an agent to be assessed;
 b) maintaining the combination produced in (a) under conditions appropriate for binding of GDF-9 to receptors on the granulosa cells wherein expression of a gene within a granulosa cell is modulated due to the binding of GDF-9 to the cells; and
 c) determining the extent to which expression of the gene regulated by binding of GDF-9 to the receptors occurs upon binding of GDF-9 to the receptors on the granulosa cells,
wherein enhanced expression of the gene upon binding of GDF-9 to the receptors in the presence of the agent to be assessed indicates that the agent enhances fertility.

29. The method of claim 28 wherein the extent to which expression of the gene occurs is determined by measuring the gene product.

30. The method of claim 29 wherein the gene encodes a protein selected from the group consisting of: hyaluronan synthase, steroidogenic acute regulatory protein, luteinizing hormone receptor, cyclooxygenase 2, activin/inhibin βB and follistatin.

31. The method of claim 28 wherein the extent to which expression of the gene occurs is determined by measuring a product or function which results from the activity of the gene of b).

32. The method of claim 31 wherein the product or function is selected from the group consisting of: hyaluronic acid, phosphorylated steroidogenic acute regulatory protein, progesterone, prostaglandins, activin βB:activin βB, inhibin α:activin βB, products produced as a result of the binding of luteinizing hormone receptor and the binding of ligand to the luteinizing hormone receptor.

33. The method of claim 28 further comprising a step (d) of comparing the extent of expression in (c) with the extent to which expression occurs in a control sample.

34. A method of identifying an agent which enhances fertility comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the granulosa cells wherein expression of a uPA gene is modulated due to the binding of GDF-9 to the cells; and
   c) determining the extent to which expression of the uPA gene regulated by binding of GDF-9 to the receptors occurs upon binding of GDF-9 to the receptors on the granulosa cells,
wherein a decrease in production of uPA in the presence of high concentrations of GDF-9 indicates that the agent enhances fertility.

35. A method of identifying an agent which alters folliculogenesis comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the cells wherein expression of the gene is modulated due to the binding of GDF-9 to the cells; and
   c) determining the extent to which expression of the gene regulated by binding of GDF-9 to the receptors occurs upon binding of GDF-9 to the receptors;
      wherein alteration of expression of the gene upon binding of GDF-9 to the receptors in the presence of the agent to be assessed indicates that the agent alters folliculogenesis.

36. The method of claim 35 wherein the gene encodes a protein selected from the group consisting of: hyaluronan synthase, steroidogenic acute regulatory protein, luteinizing hormone receptor, cyclooxygenase 2, urokinase plasminogen activator, kit ligand, activin/inhibin βB and follistatin.

37. A method of identifying an agent which alters activity of growth differentiation factor 9 (GDF-9) comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and
   c) determining the extent to which expression of the gene regulated by binding of GDF-9 to the receptors occurs upon binding of GDF-9 to the receptors;
wherein alteration of expression of the gene upon binding of GDF-9 to the receptors in the presence of the agent to be assessed indicates that the agent alters GDF-9 activity.

38. The method of claim 37, wherein the extent to which expression of the gene occurs is determined by measuring the gene product or function which results from the activity of the gene in b).

39. A method of identifying an agent which is an inhibitor of growth differentiation factor 9 (GDF-9) comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and
   c) determining the extent to which expression of the gene regulated by binding of GDF-9 to the receptors occurs upon binding of GDF-9 to the receptors;
wherein inhibition of expression of the gene upon binding of GDF-9 to the receptors in the presence of the agent to be assessed indicates that the agent inhibits GDF-9 activity.

40. A method of identifying an agent which is an enhancer of growth differentiation factor 9 (GDF-9) comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and
   c) determining the extent to which expression of the gene regulated by binding of GDF-9 to the receptors occurs upon binding of GDF-9 to the receptors;
wherein enhancement of expression of the gene upon binding of GDF-9 to the receptors in the presence of the agent to be assessed indicates that the agent enhances GDF-9 activity.

41. A method of identifying an agent which inhibits female fertility comprising the steps of:
   a) combining:
      i) granulosa cells;
      ii) GDF-9; and
      iii) an agent to be assessed;
   b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and c) determining the extent to which expression of the gene regulated by binding of GDF-9 to the receptors occurs upon binding of GDF-9 to the receptors;

wherein alteration of expression of the gene upon binding of GDF-9 to the receptors in the presence of the agent to be assessed indicates that the agent inhibits female fertility.

42. A method of identifying an agent which enhances female fertility comprising the steps of:
  a) combining:
    i) granulosa cells;
    ii) GDF-9; and
    iii) an agent to be assessed;
  b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and
  c) determining the extent to which expression of the gene regulated by binding of GDF-9 to the receptors occurs upon binding of GDF-9 to the receptors;

wherein alteration of expression of the gene upon binding of GDF-9 to the receptors in the presence of the agent to be assessed indicates that the agent enhances female fertility.

43. A method of identifying an agent which alters folliculogenesis comprising the steps of:
  a) combining:
    i) granulosa cells;
    ii) GDF-9; and
    iii) an agent to be assessed;
  b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof, is modulated due to the binding of GDF-9 to the cells; and
  c) determining the extent to which expression of the gene regulated by binding of GDF-9 to the receptors occurs upon binding of GDF-9 to the receptors;

wherein alteration of expression of the gene upon binding of GDF-9 to the receptors in the presence of the agent to be assessed indicates that the agent alters folliculogenesis.

44. A method of identifying an agent which is an agonist of GDF-9 comprising the steps of:
  a) combining:
    i) granulosa cells; and
    ii) an agent to be assessed;
  b) maintaining the combination produced in (a) under conditions appropriate for binding of GDF-9 to receptors on the cells wherein expression of a gene selected from the group consisting of: hyaluronan synthase, steroidogenic acute regulatory protein, luteinizing hormone receptor, cyclooxygenase 2, urokinase plasminogen activator, kit ligand, activin/inhibin βB, follistatin and a combination thereof is modulated due to the binding of GDF-9 to the cells; and
  c) determining the extent to which expression of the gene regulated by binding of GDF-9 to the receptors occurs, wherein expression of the gene in the presence of the agent to be assessed indicates that the agent is an agonist of GDF-9.

45. A method of identifying an agent which alters folliculogenesis comprising the steps of:
  a) combining:
    i) granulosa cells, and a uPA gene, wherein expression of the gene is regulated by binding of GDF-9 to receptors of the cell;
    ii) GDF-9; and
    iii) an agent to be assessed,
  b) maintaining the combination produced in a) under conditions appropriate for binding of the agent to receptors on the cells wherein expression of the uPA gene is modulated due to the binding of GDF-9 to the cells; and
  c) determining the extent to which binding of the agent to the receptors on the cells occurs, wherein binding of the agent to the GDF-9 receptors indicates that the agent alters folliculogenesis.

46. The method of claim 1 wherein the granulosa cells are selected from the group consisting of: mural granulosa and cumulus cells.

47. The method of claim 7 wherein the granulosa cells are selected from the group consisting of: mural granulosa and cumulus cells.

48. The method of claim 14 wherein the granulosa cells are selected from the group consisting of: mural granulosa and cumulus cells.

49. The method of claim 21 wherein the granulosa cells are selected from the group consisting of: mural granulosa and cumulus cells.

50. The method of claim 28 wherein the granulosa cells are selected from the group consisting of: mural granulosa and cumulus cells.

51. The method of claim 35 wherein the granulosa cells are selected from the group consisting of: mural granulosa and cumulus cells.

* * * * *

SEQUENCE LISTING

<160> NUMBER OF SEQ ID NOS: 18

<210> SEQ ID NO 1
<211> LENGTH: 23
<212> TYPE: DNA
<213> ORGANISM: Unknown
<220> FEATURE:
<223> OTHER INFORMATION: Artificial Sequence

<400> SEQUENCE: 1 gcttgaccctgcctcatctg tgg                23

<210> SEQ ID NO 2
<211> LENGTH: 23
<212> TYPE: DNA
<213> ORGANISM: Unknown
<220> FEATURE:
<223> OTHER INFORMATION: Artificial Sequence

<400> SEQUENCE: 2
ctggttcagc catctcagat att                23

<210> SEQ ID NO 3
<211> LENGTH: 23
<212> TYPE: DNA
<213> ORGANISM: Unknown
<220> FEATURE:
<223> OTHER INFORMATION: Artificial Sequence

<400> SEQUENCE: 3
catgtttgtg atgggtgtga acc                23

<210> SEQ ID NO 4
<211> LENGTH: 23
<212> TYPE: DNA
<213> ORGANISM: Unknown
<220> FEATURE:
<223> OTHER INFORMATION: Artificial Sequence

<400> SEQUENCE: 4
tgggagttgc tgttgaagtc gca                23

<210> SEQ ID NO 5

```
<211> LENGTH: 20
<212> TYPE: DNA
<213> ORGANISM: Unknown
<220> FEATURE:
<223> OTHER INFORMATION: Artificial Sequence

<400> SEQUENCE: 5
cctggttaag cagtacagcc                                              20

<210> SEQ ID NO 6
<211> LENGTH: 20
<212> TYPE: DNA
<213> ORGANISM: Unknown
<220> FEATURE:
<223> OTHER INFORMATION: Artificial Sequence

<400> SEQUENCE: 6
tactaggcag atggccacag                                              20

<210> SEQ ID NO 7
<211> LENGTH: 22
<212> TYPE: DNA
<213> ORGANISM: Unknown
<220> FEATURE:
<223> OTHER INFORMATION: Artificial Sequence

<400> SEQUENCE: 7
gttcagactg tgagatcact gg                                           22

<210> SEQ ID NO 8
<211> LENGTH: 21
<212> TYPE: DNA
<213> ORGANISM: Unknown
<220> FEATURE:
<223> OTHER INFORMATION: Artificial Sequence

<400> SEQUENCE: 8
cagagaggac ggtcagcatg g                                            21

<210> SEQ ID NO 9
<211> LENGTH: 22
<212> TYPE: DNA
<213> ORGANISM: Unknown
<220> FEATURE:
<223> OTHER INFORMATION: Artificial Sequence

<400> SEQUENCE: 9
tcgcttggag gtggtggtag ac                                           22

<210> SEQ ID NO 10
<211> LENGTH: 22
<212> TYPE: DNA
<213> ORGANISM: Unknown
<220> FEATURE:
<223> OTHER INFORMATION: Artificial Sequence

<400> SEQUENCE: 10
gcaggtcaat gtggtggaca gt                                           22

<210> SEQ ID NO 11
<211> LENGTH: 19
<212> TYPE: DNA
<213> ORGANISM: Unknown
<220> FEATURE:
<223> OTHER INFORMATION: Artificial Sequence

<400> SEQUENCE: 11
```

```
gccaacatta ccgagatgc                                                    19

<210> SEQ ID NO 12
<211> LENGTH: 20
<212> TYPE: DNA
<213> ORGANISM: Unknown
<220> FEATURE:
<223> OTHER INFORMATION: Artificial Sequence

<400> SEQUENCE: 12
cgaacacccc agccaaagcc                                                   20

<210> SEQ ID NO 13
<211> LENGTH: 22
<212> TYPE: DNA
<213> ORGANISM: Unknown
<220> FEATURE:
<223> OTHER INFORMATION: Artificial Sequence

<400> SEQUENCE: 13
ctccttttca accagcagtt cc                                                22

<210> SEQ ID NO 14
<211> LENGTH: 22
<212> TYPE: DNA
<213> ORGANISM: Unknown
<220> FEATURE:
<223> OTHER INFORMATION: Artificial Sequence

<400> SEQUENCE: 14
tctgcagcca tttccttctc tc                                                22

<210> SEQ ID NO 15
<211> LENGTH: 23
<212> TYPE: DNA
<213> ORGANISM: Unknown
<220> FEATURE:
<223> OTHER INFORMATION: Artificial Sequence

<400> SEQUENCE: 15
cttatacata accaccatac cag                                               23

<210> SEQ ID NO 16
<211> LENGTH: 22
<212> TYPE: DNA
<213> ORGANISM: Unknown
<220> FEATURE:
<223> OTHER INFORMATION: Artificial Sequence

<400> SEQUENCE: 16
atcccagcca ctgagttcat tc                                                22

<210> SEQ ID NO 17
<211> LENGTH: 24
<212> TYPE: DNA
<213> ORGANISM: Unknown
<220> FEATURE:
<223> OTHER INFORMATION: Artificial Sequence

<400> SEQUENCE: 17
ccagaaacta gatcctttac tcct                                              24

<210> SEQ ID NO 18
<211> LENGTH: 22
<212> TYPE: DNA
```

-continued

<213> ORGANISM: Unknown
<220> FEATURE:
<223> OTHER INFORMATION: Artificial Sequence

<400> SEQUENCE: 18
ctgttgcagc cagctccctt ag                                                  22